United States Patent
Swartz et al.

(10) Patent No.: US 10,221,401 B2
(45) Date of Patent: Mar. 5, 2019

(54) OXYGEN TOLERANT HYDROGENASE BY MUTATING ELECTRON SUPPLY PATHWAY

(71) Applicant: The Board of Trustees of the Leland Stanford Junior University, Stanford, CA (US)

(72) Inventors: James Robert Swartz, Menlo Park, CA (US); Jamin Koo, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 365 days.

(21) Appl. No.: 15/255,833

(22) Filed: Sep. 2, 2016

(65) Prior Publication Data
US 2017/0067034 A1     Mar. 9, 2017

Related U.S. Application Data

(60) Provisional application No. 62/215,522, filed on Sep. 8, 2015.

(51) Int. Cl.
| C12N 9/02 | (2006.01) |
| C12P 3/00 | (2006.01) |

(52) U.S. Cl.
CPC .............. *C12N 9/0067* (2013.01); *C12P 3/00* (2013.01); *C12Y 112/02001* (2013.01); *C12Y 112/07002* (2013.01)

(58) Field of Classification Search
None
See application file for complete search history.

(56) References Cited

U.S. PATENT DOCUMENTS

| 6,337,191 | B1 | 1/2002 | Swartz et al. |
| 7,351,563 | B2 | 4/2008 | Swartz et al. |
| 2002/0081660 | A1 | 6/2002 | Swartz et al. |
| 2004/0209321 | A1 | 10/2004 | Swartz et al. |
| 2009/0263846 | A1* | 10/2009 | King ............ C12N 9/001 435/25 |

FOREIGN PATENT DOCUMENTS

| WO | 2000/55353 A1 | 9/2000 |
| WO | 2004/016778 A1 | 2/2004 |
| WO | 2005/010155 A2 | 2/2005 |

OTHER PUBLICATIONS

Posewitz et al., "Discovery of Two Novel Radical S-Adenosylmethionine Proteins Required for the Assembly of an Active [Fe] Hydrogenase", J Biol Chem., Jun. 11, 2004, pp. 25711-25720, 279(24), ASBMB, Rockville, MD.

* cited by examiner

*Primary Examiner* — Suzanne M Noakes
*Assistant Examiner* — Jae W Lee
(74) *Attorney, Agent, or Firm* — Pamela J. Sherwood; Bozicevic, Field & Francis LLP

(57) ABSTRACT

Compositions and methods are provided for an $O_2$ tolerant Fe—Fe hydrogenase. The hydrogenases of the invention comprise specific amino acid substitutions relative to the native, or wild-type enzymes.

6 Claims, 9 Drawing Sheets
(8 of 9 Drawing Sheet(s) Filed in Color)
Specification includes a Sequence Listing.

SEQUENCE LISTING

```
<160> NUMBER OF SEQ ID NOS: 6

<210> SEQ ID NO 1
<211> LENGTH: 574
<212> TYPE: PRT
<213> ORGANISM: Clostridium pasteurianum

<400> SEQUENCE: 1

Met Lys Thr Ile Ile Ile Asn Gly Val Gln Phe Asn Thr Asp Glu Asp
 1               5                  10                  15

Thr Thr Ile Leu Lys Phe Ala Arg Asp Asn Asn Ile Asp Ile Ser Ala
                20                  25                  30

Leu Cys Phe Leu Asn Asn Cys Asn Asn Asp Ile Asn Lys Cys Glu Ile
            35                  40                  45

Cys Thr Val Glu Val Glu Gly Thr Gly Leu Val Thr Ala Cys Asp Thr
        50                  55                  60
```

-continued

Leu Ile Glu Asp Gly Met Ile Ile Asn Thr Asn Ser Asp Ala Val Asn
65                  70                  75                  80

Glu Lys Ile Lys Ser Arg Ile Ser Gln Leu Leu Asp Ile His Glu Phe
            85                  90                  95

Lys Cys Gly Pro Cys Asn Arg Arg Glu Asn Cys Glu Phe Leu Lys Leu
                100                 105                 110

Val Ile Lys Tyr Lys Ala Arg Ala Ser Lys Pro Phe Leu Pro Lys Asp
        115                 120                 125

Lys Thr Glu Tyr Val Asp Glu Arg Ser Lys Ser Leu Thr Val Asp Arg
    130                 135                 140

Thr Lys Cys Leu Leu Cys Gly Arg Cys Val Asn Ala Cys Gly Lys Asn
145                 150                 155                 160

Thr Glu Thr Tyr Ala Met Lys Phe Leu Asn Lys Asn Gly Lys Thr Ile
                165                 170                 175

Ile Gly Ala Glu Asp Glu Lys Cys Phe Asp Asp Thr Asn Cys Leu Leu
        180                 185                 190

Cys Gly Gln Cys Ile Ile Ala Cys Pro Val Ala Ala Leu Ser Glu Lys
    195                 200                 205

Ser His Met Asp Arg Val Lys Asn Ala Leu Asn Ala Pro Glu Lys His
    210                 215                 220

Val Ile Val Ala Met Ala Pro Ser Val Arg Ala Ser Ile Gly Glu Leu
225                 230                 235                 240

Phe Asn Met Gly Phe Gly Val Asp Val Thr Gly Lys Ile Tyr Thr Ala
                245                 250                 255

Leu Arg Gln Leu Gly Phe Asp Lys Ile Phe Asp Ile Asn Phe Gly Ala
        260                 265                 270

Asp Met Thr Ile Met Glu Glu Ala Thr Glu Leu Val Gln Arg Ile Glu
    275                 280                 285

Asn Asn Gly Pro Phe Pro Met Phe Thr Ser Cys Cys Pro Gly Trp Val
    290                 295                 300

Arg Gln Ala Glu Asn Tyr Tyr Pro Glu Leu Leu Asn Asn Leu Ser Ser
305                 310                 315                 320

Ala Lys Ser Pro Gln Gln Ile Phe Gly Thr Ala Ser Lys Thr Tyr Tyr
                325                 330                 335

Pro Ser Ile Ser Gly Leu Asp Pro Lys Asn Val Phe Thr Val Thr Val
        340                 345                 350

Met Pro Cys Thr Ser Lys Lys Phe Glu Ala Asp Arg Pro Gln Met Glu
    355                 360                 365

Lys Asp Gly Leu Arg Asp Ile Asp Ala Val Ile Thr Thr Arg Glu Leu
    370                 375                 380

Ala Lys Met Ile Lys Asp Ala Lys Ile Pro Phe Ala Lys Leu Glu Asp
385                 390                 395                 400

Ser Glu Ala Asp Pro Ala Met Gly Glu Tyr Ser Gly Ala Gly Ala Ile
                405                 410                 415

Phe Gly Ala Thr Gly Gly Val Met Glu Ala Ala Leu Arg Ser Ala Lys
        420                 425                 430

Asp Phe Ala Glu Asn Ala Glu Leu Glu Asp Ile Glu Tyr Lys Gln Val
    435                 440                 445

Arg Gly Leu Asn Gly Ile Lys Glu Ala Glu Val Glu Ile Asn Asn Asn
    450                 455                 460

Lys Tyr Asn Val Ala Val Ile Asn Gly Ala Ser Asn Leu Phe Lys Phe
465                 470                 475                 480

Met Lys Ser Gly Met Ile Asn Glu Lys Gln Tyr His Phe Ile Glu Val

```
                      485                 490                 495
Met Ala Cys His Gly Cys Val Asn Gly Gly Gln Pro His Val
                500                 505                 510

Asn Pro Lys Asp Leu Glu Lys Val Asp Ile Lys Val Arg Ala Ser
            515                 520                 525

Val Leu Tyr Asn Gln Asp Glu His Leu Ser Lys Arg Lys Ser His Glu
        530                 535                 540

Asn Thr Ala Leu Val Lys Met Tyr Gln Asn Tyr Phe Gly Lys Pro Gly
545                 550                 555                 560

Glu Gly Arg Ala His Glu Ile Leu His Phe Lys Tyr Lys Lys
                565                 570

<210> SEQ ID NO 2
<211> LENGTH: 582
<212> TYPE: PRT
<213> ORGANISM: Clostridium acetobutylicum

<400> SEQUENCE: 2

Met Lys Thr Ile Ile Leu Asn Gly Asn Glu Val His Thr Asp Lys Asp
1               5                   10                  15

Ile Thr Ile Leu Glu Leu Ala Arg Glu Asn Asn Val Asp Ile Pro Thr
            20                  25                  30

Leu Cys Phe Leu Lys Asp Cys Gly Asn Phe Gly Lys Cys Gly Val Cys
        35                  40                  45

Met Val Glu Val Glu Gly Lys Gly Phe Arg Ala Ala Cys Val Ala Lys
    50                  55                  60

Val Glu Asp Gly Met Val Ile Asn Thr Glu Ser Asp Glu Val Lys Glu
65                  70                  75                  80

Arg Ile Lys Lys Arg Val Ser Met Leu Leu Asp Lys His Glu Phe Lys
                85                  90                  95

Cys Gly Gln Cys Ser Arg Arg Glu Asn Cys Glu Phe Leu Lys Leu Val
            100                 105                 110

Ile Lys Thr Lys Ala Lys Ala Ser Lys Pro Phe Leu Pro Glu Asp Lys
        115                 120                 125

Asp Ala Leu Val Asp Asn Arg Ser Lys Ala Ile Val Ile Asp Arg Ser
    130                 135                 140

Lys Cys Val Leu Cys Gly Arg Cys Val Ala Ala Cys Lys Gln His Thr
145                 150                 155                 160

Ser Thr Cys Ser Ile Gln Phe Ile Lys Lys Asp Gly Gln Arg Ala Val
                165                 170                 175

Gly Thr Val Asp Asp Val Cys Leu Asp Asp Ser Thr Cys Leu Leu Cys
            180                 185                 190

Gly Gln Cys Val Ile Ala Cys Pro Val Ala Ala Leu Lys Glu Lys Ser
        195                 200                 205

His Ile Glu Lys Val Gln Glu Ala Leu Asn Asp Pro Lys Lys His Val
    210                 215                 220

Ile Val Ala Met Ala Pro Ser Val Arg Thr Ala Met Gly Glu Leu Phe
225                 230                 235                 240

Lys Met Gly Tyr Gly Lys Asp Val Thr Gly Lys Leu Tyr Thr Ala Leu
                245                 250                 255

Arg Met Leu Gly Phe Asp Lys Val Phe Asp Ile Asn Phe Gly Ala Asp
            260                 265                 270

Met Thr Ile Met Glu Glu Ala Thr Glu Leu Leu Gly Arg Val Lys Asn
        275                 280                 285
```

Asn Gly Pro Phe Pro Met Phe Thr Ser Cys Cys Pro Ala Trp Val Arg
    290                 295                 300

Leu Ala Gln Asn Tyr His Pro Glu Leu Leu Asp Asn Leu Ser Ser Ala
305                 310                 315                 320

Lys Ser Pro Gln Gln Ile Phe Gly Thr Ala Ser Lys Thr Tyr Tyr Pro
                325                 330                 335

Ser Ile Ser Gly Ile Ala Pro Glu Asp Val Tyr Thr Val Thr Ile Met
                340                 345                 350

Pro Cys Asn Asp Lys Lys Tyr Glu Ala Asp Ile Pro Phe Met Glu Thr
                355                 360                 365

Asn Ser Leu Arg Asp Ile Asp Ala Ser Leu Thr Thr Arg Glu Leu Ala
370                 375                 380

Lys Met Ile Lys Asp Ala Lys Ile Lys Phe Ala Asp Leu Glu Asp Gly
385                 390                 395                 400

Glu Val Asp Pro Ala Met Gly Thr Tyr Ser Gly Ala Gly Ala Ile Phe
                405                 410                 415

Gly Ala Thr Gly Gly Val Met Glu Ala Ala Ile Arg Ser Ala Lys Asp
                420                 425                 430

Phe Ala Glu Asn Lys Glu Leu Glu Asn Val Asp Tyr Thr Glu Val Arg
                435                 440                 445

Gly Phe Lys Gly Ile Lys Glu Ala Glu Val Glu Ile Ala Gly Asn Lys
450                 455                 460

Leu Asn Val Ala Val Ile Asn Gly Ala Ser Asn Phe Phe Glu Phe Met
465                 470                 475                 480

Lys Ser Gly Lys Met Asn Glu Lys Gln Tyr His Phe Ile Glu Val Met
                485                 490                 495

Ala Cys Pro Gly Gly Cys Ile Asn Gly Gly Gly Gln Pro His Val Asn
                500                 505                 510

Ala Leu Asp Arg Glu Asn Val Asp Tyr Arg Lys Leu Arg Ala Ser Val
                515                 520                 525

Leu Tyr Asn Gln Asp Lys Asn Val Leu Ser Lys Arg Lys Ser His Asp
                530                 535                 540

Asn Pro Ala Ile Ile Lys Met Tyr Asp Ser Tyr Phe Gly Lys Pro Gly
545                 550                 555                 560

Glu Gly Leu Ala His Lys Leu Leu His Val Lys Tyr Thr Lys Asp Lys
                565                 570                 575

Asn Val Ser Lys His Glu
            580

<210> SEQ ID NO 3
<211> LENGTH: 574
<212> TYPE: PRT
<213> ORGANISM: Clostridium cellulovorans

<400> SEQUENCE: 3

Met Lys Thr Ile Val Ile Asp Gly Asn Val Ile Glu Thr Ser Asp Val
1               5                   10                  15

Thr Thr Ile Leu Lys Leu Ala Lys Asp Asn Ile Asp Ile Ser Thr
            20                  25                  30

Leu Cys Phe Leu Pro Asp Cys Ile Asp Ile Gly Asn Cys Gly Val Cys
            35                  40                  45

Lys Val Glu Ile Gln Gly Arg Glu Gln Leu Val Thr Ala Cys Asn Thr
50                  55                  60

Leu Val Glu Asp Gly Met Val Ile Asp Thr Lys Ser Glu Arg Val Ala
65                  70                  75                  80

```
Glu Ala Val Lys Gly Arg Leu Ser Glu Leu Leu Asp Lys His Glu Phe
                 85                  90                  95
Lys Cys Gly Thr Cys Pro Arg Lys Glu Asn Cys Glu Phe Leu Lys Leu
            100                 105                 110
Val Ile Lys His Lys Ala Arg Ala Thr Thr Pro Phe Met Pro Lys Asp
        115                 120                 125
Lys Thr Glu Tyr Leu Asp Val Arg Ser Lys Ser Ile Ile Ile Asp Arg
    130                 135                 140
Thr Lys Cys Val Leu Cys Gly Arg Cys Glu Ala Thr Cys Glu Ser Lys
145                 150                 155                 160
Thr Gly Thr Ala Ser Ile Lys Ile Val Arg Asp Gly Asp Leu Val Arg
                165                 170                 175
Val Ser Thr Thr Asp Asp Lys Cys Phe Asp Thr Asn Cys Leu Leu
            180                 185                 190
Cys Gly Gln Cys Val Ala Val Cys Pro Val Ala Leu Ser Glu Lys
        195                 200                 205
Pro His Ile Asp Arg Val Lys Glu Ala Leu Glu Asp Pro Glu Lys His
    210                 215                 220
Val Ile Val Ala Met Ala Pro Ser Val Arg Thr Ala Leu Gly Glu Leu
225                 230                 235                 240
Phe Lys Met Gly Tyr Gly Val Asp Val Thr Gly Lys Ile Tyr Thr Ala
                245                 250                 255
Leu Lys Glu Leu Gly Phe Asn Arg Ile Phe Asp Ile Asn Phe Gly Ala
            260                 265                 270
Asp Met Thr Ile Met Glu Glu Ala Thr Glu Leu Ile Gln Arg Ile Asn
        275                 280                 285
Asn Asn Gly Pro Phe Pro Met Phe Thr Ser Cys Cys Pro Gly Trp Val
    290                 295                 300
Arg Gln Ala Glu Asn Tyr Tyr Pro Glu Leu Leu Ser Asn Leu Ser Ser
305                 310                 315                 320
Ala Lys Ser Pro Gln Gln Ile Phe Gly Ala Ala Thr Lys Ser Tyr Tyr
                325                 330                 335
Pro Ser Ile Ser Asp Ile Asp Pro Ser Lys Ile Phe Thr Val Thr Ile
            340                 345                 350
Met Pro Cys Thr Ala Lys Lys Tyr Glu Ala Asp Arg Pro Glu Met Glu
        355                 360                 365
Asn Asp Gly Leu Arg Asn Ile Asp Ala Val Ile Thr Thr Arg Glu Leu
    370                 375                 380
Ala Lys Met Val Lys Asp Ala Lys Ile Asn Phe Ala Thr Leu Glu Asp
385                 390                 395                 400
Gly Glu Cys Asp Leu Ala Met Gly Glu Tyr Thr Gly Ala Gly Thr Ile
                405                 410                 415
Phe Gly Ala Thr Gly Gly Val Met Glu Ala Ala Leu Arg Thr Ala Lys
            420                 425                 430
Asp Phe Val Glu Lys Ala Asp Leu His Asp Ile Glu Tyr Glu Ala Val
        435                 440                 445
Arg Gly Leu Asn Gly Ile Lys Glu Ala Thr Val Glu Ile Gly Gly Ser
    450                 455                 460
Glu Tyr Asn Val Ala Val Ile Asn Gly Ser Val Asn Val Phe Glu Phe
465                 470                 475                 480
Ile Lys Ser Gly Ala Leu Asp Arg Lys Gln Tyr His Phe Ile Glu Val
                485                 490                 495
```

```
Met Ala Cys Pro Gly Gly Cys Val Asn Gly Gly Gln Pro His Val
            500                 505                 510

Pro Val Ala Asp Arg Met Asp Met Asp Ile Arg Leu Val Arg Ala Ser
        515                 520                 525

Val Leu Tyr Asn Gln Asp Lys Asn Leu Pro Lys Arg Lys Ser His Glu
        530                 535                 540

Asn Glu Ala Leu Lys Arg Met Tyr Asp Ser Tyr Tyr Gly Thr Pro Gly
545                 550                 555                 560

Glu Gly Leu Ala His Lys Leu Leu His Val Lys Tyr Lys Lys
                565                 570

<210> SEQ ID NO 4
<211> LENGTH: 582
<212> TYPE: PRT
<213> ORGANISM: Clostridium paraputrificum

<400> SEQUENCE: 4

Met Lys Asn Ile Ile Ile Asn Asp Lys Val Cys Lys Ala Ala Glu Gly
  1               5                  10                  15

Lys Thr Val Leu Glu Val Ala Arg Glu Asn Gly Ile Asp Ile Pro Thr
             20                  25                  30

Leu Cys Tyr Leu Lys Glu Cys Gly Asn Val Gly Lys Cys Gly Val Cys
         35                  40                  45

Ala Val Glu Ile Glu Gly Lys Asn Asn Leu Ala Leu Ala Cys Leu Thr
     50                  55                  60

Lys Val Glu Asp Gly Met Val Val Arg Thr Asp Thr Glu Lys Val Gln
 65                  70                  75                  80

Glu Arg Val Lys Ser Arg Val Ser Thr Ile Leu Asn Lys His Glu Phe
                 85                  90                  95

Lys Cys Gly Pro Cys Pro Arg Glu Asn Cys Glu Leu Leu Lys Leu
            100                 105                 110

Val Ile Lys Thr Lys Ala Lys Ala Thr Thr Pro Phe Val Val Glu Asn
            115                 120                 125

Lys Glu Glu Tyr Val Asp Ile Arg Ser Lys Ser Ile Thr Ile Asp Arg
        130                 135                 140

Ser Lys Cys Ile Leu Cys Gly Arg Cys Ala Ala Cys Thr Glu Lys
145                 150                 155                 160

Thr Gly Thr Ser Ser Ile Lys Leu Val Asn Val Asn Gly Lys Arg Ile
                165                 170                 175

Val Thr Pro Glu Glu Gln Lys Cys Phe Asp Glu Thr Asn Cys Leu Leu
            180                 185                 190

Cys Gly Gln Cys Val Ala Ala Cys Pro Val Gly Ala Leu Ser Glu Lys
        195                 200                 205

Thr His Ile Asp Arg Val Lys Glu Ala Leu Glu Asp Pro Glu Lys His
    210                 215                 220

Val Ile Val Ala Met Ala Pro Ala Val Arg Thr Ala Met Gly Glu Leu
225                 230                 235                 240

Phe Asn Met Gly Tyr Gly Val Asp Val Thr Gly Lys Leu Tyr Thr Ala
                245                 250                 255

Leu Arg Glu Leu Gly Phe Asp Arg Ile Phe Asp Ile Asn Phe Gly Ala
            260                 265                 270

Asp Met Thr Ile Met Glu Glu Ala Thr Glu Leu Leu Glu Arg Ile Glu
        275                 280                 285

Lys Lys Gly Pro Phe Pro Met Phe Thr Ser Cys Cys Pro Gly Trp Val
    290                 295                 300
```

```
Arg Gln Val Glu Asn Tyr Tyr Pro Glu Leu Leu Glu Asn Leu Ser Ser
305                 310                 315                 320

Ala Lys Ser Pro Gln Gln Ile Phe Gly Thr Ala Ser Lys Thr Tyr Tyr
                325                 330                 335

Pro His Ile Ala Gly Ile Asp Pro Glu Lys Ile Phe Thr Val Thr Ile
            340                 345                 350

Met Pro Cys Thr Ala Lys Lys Phe Glu Ala Asp Arg Glu Asp Met Glu
        355                 360                 365

Leu Asp Gly Leu Arg Asn Ile Asp Ala Val Leu Thr Thr Arg Glu Leu
370                 375                 380

Ala Lys Phe Ile Lys Glu Lys Ile Ala Phe Ala Lys Leu Glu Asp
385                 390                 395                 400

Ser Glu Ala Asp Pro Ala Met Gly Glu Tyr Thr Gly Ala Gly Val Ile
                405                 410                 415

Phe Gly Ala Thr Gly Gly Val Met Glu Ala Ala Ile Arg Thr Ala Lys
            420                 425                 430

Glu Phe Val Glu Lys Lys Glu Leu Glu Asn Leu Asp Tyr Thr Glu Val
        435                 440                 445

Arg Gly Leu Asn Gly Ile Lys Glu Ala Ser Val Asn Ile Gly Gly Glu
    450                 455                 460

Asp Tyr Asn Val Ala Val Ile Asn Gly Ser Ala Asn Leu Phe Glu Phe
465                 470                 475                 480

Ile Glu Ser Gly Arg Met Asn Ser Lys Glu Tyr His Phe Ile Glu Val
                485                 490                 495

Met Thr Cys Pro Gly Gly Cys Val Asn Gly Gly Gly Gln Pro His Val
            500                 505                 510

Asn Asn Leu Glu Arg Glu Lys Ile Asp Ile Lys Ser Val Arg Ala Ser
        515                 520                 525

Val Leu Tyr Asn Gln Asp Lys Ser Ala Lys Lys Arg Lys Ser His Glu
    530                 535                 540

Asn Val Ala Leu Met Lys Met Tyr Asp Glu Tyr Met Gly Gln Pro Gly
545                 550                 555                 560

Arg Gly Lys Ala His Glu Leu Leu His Tyr Lys Tyr Lys Lys Glu
                565                 570                 575

Thr Ser Glu Glu Val Ile
            580

<210> SEQ ID NO 5
<211> LENGTH: 580
<212> TYPE: PRT
<213> ORGANISM: Clostridium kluyveri DSM 555

<400> SEQUENCE: 5

Met Ile Thr Val Ile Leu Asp Gly Lys Glu Ile Lys Ala Lys Glu Asn
1               5                   10                  15

Ser Thr Ile Leu Gln Val Ala Arg Asp Asn Val Asp Ile Pro Thr
            20                  25                  30

Leu Cys Tyr Leu Lys Asp Cys Met Asn Ile Gly Lys Cys Gly Val Cys
        35                  40                  45

Leu Val Glu Ala Asn Gly Lys Ile Val Ala Cys Ala Thr Lys Ile
    50                  55                  60

Glu Glu Gly Met Val Ile Asp Thr Lys Ser Glu Thr Val Lys Glu Arg
65                  70                  75                  80

Ile Lys Lys Arg Ile Ser Ser Leu Leu Asp Thr His Glu Phe Lys Cys
```

-continued

```
                    85                  90                  95
Gly Pro Cys Pro Arg Glu Asp Cys Glu Phe Leu Lys Leu Val Ile
                100                 105                 110
Lys Thr Lys Ala Lys Ala Ser Lys Pro Phe Leu Pro Glu Asp Arg Glu
        115                 120                 125
Lys Tyr Ile Asp Ser Arg Ser Asn Ala Leu Val Leu Asp Arg Thr Lys
130                 135                 140
Cys Ile Leu Cys Gly Arg Cys Val Ala Cys Lys Val His Ser Gly
145                 150                 155                 160
Thr Ser Val Met Gln Phe Ile Lys Lys Asp Gly Lys Arg Thr Val Gly
                165                 170                 175
Ile Glu Asn Asn Pro Cys Phe Asp Asn Ser Asn Cys Leu Leu Cys Gly
                180                 185                 190
Gln Cys Val Ile Ala Cys Pro Val Gly Ala Leu Thr Glu Lys Pro His
            195                 200                 205
Ile Ser Arg Val Gln Glu Ala Leu Lys Asp Pro Lys Lys His Val Ile
            210                 215                 220
Val Ala Met Ala Pro Ser Val Arg Ala Ala Ile Gly Glu Leu Phe Asn
225                 230                 235                 240
Met Gly Phe Gly Lys Asp Val Thr Gly Lys Ile Tyr Thr Ala Leu Arg
                245                 250                 255
Met Leu Asn Phe Asp Lys Ile Phe Asp Ile Asn Phe Gly Ala Asp Met
                260                 265                 270
Thr Ile Met Glu Glu Ala Thr Glu Leu Leu Glu Arg Ile Lys Asn Gly
            275                 280                 285
Gly Pro Phe Pro Met Phe Thr Ser Cys Cys Pro Ala Trp Val Arg Gln
            290                 295                 300
Ala Gln Asn Tyr Tyr Pro Glu Leu Leu Glu Asn Leu Ser Ser Ala Lys
305                 310                 315                 320
Ser Pro Gln Gln Ile Phe Gly Thr Ala Thr Lys Thr Tyr Tyr Pro Ser
                325                 330                 335
Ile Ser Gly Ile Glu Ala Lys Asp Ile Tyr Thr Val Thr Ile Met Pro
            340                 345                 350
Cys Asn Asp Lys Lys Tyr Glu Ala Asp Leu Thr Asp Met Glu Val Asn
            355                 360                 365
Gly Met Arg Cys Ile Asp Ala Val Leu Thr Thr Arg Glu Leu Ala Lys
            370                 375                 380
Met Ile Lys Ala Ala Lys Ile Lys Phe Thr Ser Leu Glu Asp Ser Glu
385                 390                 395                 400
Ala Asp Ala Ala Met Gly Glu Tyr Ser Gly Ala Gly Val Ile Phe Gly
                405                 410                 415
Asn Thr Gly Gly Val Met Glu Ala Ala Leu Arg Thr Ala Lys Asp Phe
            420                 425                 430
Ala Glu Asn Val Asp Leu Lys Asp Ile Glu Tyr Thr Gln Ile Arg Gly
            435                 440                 445
Leu Lys Gly Ile Lys Glu Ser Ser Val Glu Ile Ser Gly Asn Thr Tyr
            450                 455                 460
Asn Ile Ala Val Ile Asn Gly Ala Ala Asn Leu Phe Asp Phe Ile Asp
465                 470                 475                 480
Ser Gly Lys Ile Gly Glu Lys Gln Tyr His Phe Ile Glu Val Met Ala
                485                 490                 495
Cys Pro Gly Gly Cys Ile Asn Gly Gly Gln Pro His Leu Asn Ser
            500                 505                 510
```

```
Leu Asn Arg Glu Leu Ile Asp Tyr Arg Thr Leu Arg Ala Ser Val Leu
            515                 520                 525

Tyr Asn Gln Asp Asn His Leu Pro Lys Arg Lys Ser His Lys Asn Thr
        530                 535                 540

Ala Ile Ile Lys Met Tyr Asp Thr Tyr Phe Gly Lys Pro Gly His Gly
545                 550                 555                 560

Leu Ala His Glu Leu Leu His Phe Lys Tyr Thr Glu Asp Ser Ser Glu
            565                 570                 575

Ser Lys Ile Val
            580

<210> SEQ ID NO 6
<211> LENGTH: 574
<212> TYPE: PRT
<213> ORGANISM: Clostridium pasteurianum

<400> SEQUENCE: 6

Met Lys Thr Ile Ile Asn Gly Val Gln Phe Asn Thr Asp Glu Asp
  1               5                  10                  15

Thr Thr Ile Leu Lys Phe Ala Arg Asp Asn Asn Ile Asp Ile Ser Ala
            20                  25                  30

Leu Cys Phe Leu Asn Asn Cys Asn Asn Asp Ile Asn Lys Cys Glu Ile
            35                  40                  45

Cys Thr Val Glu Val Glu Gly Thr Gly Leu Val Thr Ala Cys Asp Thr
        50                  55                  60

Leu Ile Glu Asp Gly Met Ile Ile Asn Thr Asn Ser Asp Ala Val Asn
65                  70                  75                  80

Glu Lys Ile Lys Ser Arg Ile Ser Gln Leu Leu Asp Ile His Glu Phe
                85                  90                  95

Lys Cys Gly Pro Cys Asn Arg Arg Glu Asn Cys Glu Phe Leu Lys Leu
            100                 105                 110

Val Ile Lys Tyr Lys Ala Arg Ala Ser Lys Pro Phe Leu Pro Lys Asp
            115                 120                 125

Lys Thr Glu Tyr Val Asp Glu Arg Ser Lys Ser Leu Thr Val Asp Arg
        130                 135                 140

Thr Lys Cys Leu Leu Cys Gly Arg Cys Val Asn Ala Cys Gly Lys Asn
145                 150                 155                 160

Thr Glu Thr Tyr Ala Met Lys Phe Leu Asn Lys Asn Gly Lys Thr Ile
                165                 170                 175

Ile Gly Ala Glu Asp Glu Lys Cys Phe Asp Asp Thr Asn Cys Leu Leu
            180                 185                 190

Cys Gly Gln Cys Ile Ile Ala Cys Pro Val Ala Ala Leu Ser Glu Lys
            195                 200                 205

Ser His Met Asp Arg Val Lys Asn Ala Leu Asn Ala Pro Glu Lys His
        210                 215                 220

Val Ile Val Ala Met Ala Pro Ser Val Arg Ala Ser Ile Gly Glu Leu
225                 230                 235                 240

Phe Asn Met Gly Phe Gly Val Asp Val Thr Gly Lys Ile Tyr Thr Ala
                245                 250                 255

Leu Arg Gln Leu Gly Phe Asp Lys Ile Phe Asp Ile Asn Phe Gly Ala
            260                 265                 270

Asp Met Thr Ile Met Glu Glu Ala Thr Glu Leu Val Gln Arg Ile Glu
        275                 280                 285

Asn Asn Gly Pro Phe Pro Met Phe Thr Ser Cys Cys Pro Gly Trp Val
```

```
                290                 295                 300
Arg Gln Ala Glu Asn Tyr Tyr Pro Glu Leu Leu Asn Asn Leu Ser Ser
305                     310                 315                 320

Ala Lys Ser Pro Gln Gln Ile Phe Gly Thr Ala Ser Lys Thr Tyr Tyr
                    325                 330                 335

Pro Ser Ile Ser Gly Leu Asp Pro Lys Asn Val Phe Thr Val Thr Val
                340                 345                 350

Met Pro Cys Val Thr Lys Lys Phe Glu Ala Asp Arg Pro Gln Met Glu
            355                 360                 365

Lys Asp Gly Leu Arg Asp Ile Asp Ala Val Ile Thr Thr Arg Glu Leu
    370                 375                 380

Ala Lys Met Ile Lys Asp Ala Lys Ile Pro Phe Ala Lys Leu Glu Asp
385                 390                 395                 400

Ser Glu Ala Asp Pro Ala Met Gly Glu Tyr Ser Gly Ala Gly Ala Ile
                405                 410                 415

Phe Gly Ala Thr Gly Gly Val Met Glu Ala Ala Leu Arg Ser Ala Lys
                420                 425                 430

Asp Phe Ala Glu Asn Ala Glu Leu Glu Asp Ile Glu Tyr Lys Gln Val
            435                 440                 445

Arg Gly Leu Asn Gly Ile Lys Glu Ala Glu Val Glu Ile Asn Asn Asn
    450                 455                 460

Lys Tyr Asn Val Ala Val Ile Asn Gly Ala Ser Asn Leu Phe Lys Phe
465                 470                 475                 480

Met Lys Ser Gly Met Ile Asn Glu Lys Gln Tyr His Phe Ile Glu Val
                485                 490                 495

Met Ala Cys His Gly Gly Cys Val Asn Gly Gly Gln Pro His Val
            500                 505                 510

Asn Pro Lys Asp Leu Glu Lys Val Asp Ile Lys Lys Val Arg Ala Ser
            515                 520                 525

Val Leu Tyr Asn Gln Asp Glu His Leu Ser Lys Arg Lys Ser His Glu
    530                 535                 540

Asn Thr Ala Leu Val Lys Met Tyr Gln Asn Tyr Phe Gly Lys Pro Gly
545                 550                 555                 560

Glu Gly Arg Ala His Glu Ile Leu His Phe Lys Tyr Lys Lys
                565                 570
```

OXYGEN TOLERANT HYDROGENASE BY MUTATING ELECTRON SUPPLY PATHWAY

CROSS REFERENCE

This application claims benefit of U.S. Provisional Patent Application No. 62/215,522, filed Sep. 8, 2015, which application is incorporated herein by reference in it's entirety.

FEDERALLY SPONSORED RESEARCH AND DEVELOPMENT

This invention was made with Government support under contract DE-SC0002010 awarded by the Department of Energy. The Government has certain rights in the invention.

BACKGROUND OF THE INVENTION

Current traditional energy technologies rely on fossil fuels. Their most significant limitations are the depletion of limited fossil fuel reservoirs, thus, making this a non-sustainable technology, and the net generation of $CO_2$ and other greenhouse gases, thereby affecting the global climate in a fundamental and uncontrollable manner. Hydrogen gas is a renewable energy source that does not evolve the "greenhouse gas" $CO_2$ in combustion, liberates large amounts of energy per unit weight in combustion, and is easily converted to electricity by fuel cells.

However, current sources of $H_2$ often rely on fossil fuels as input material. The use of $H_2$ as a large scale fuel therefore depends, in part, on developing new $H_2$ sources. One path of particular interest is biological $H_2$ production from sunlight, enabled by genetically engineered photosynthetic microbes that express hydrogenases—enzymes that catalyze the reversible reduction of protons into $H_2$.

Biological $H_2$ production has several advantages over $H_2$ production by photoelectrochemical or thermochemical processes. Biological $H_2$ production by photosynthetic microorganisms, for example, requires the use of a simple solar reactor such as a transparent closed box, with low energy requirements. An ideal process to produce $H_2$ more economically would be to use water as an input, and photosynthetic processes to generate the energy needed for reduction of protons to form $H_2$.

Naturally occurring photosynthetic organisms are unable to meet this need. Cyanobacteria such *Synechocystis* species have both photosystem I (PS I) and photosystem II (PS II) and can oxidize water to generate photoreductants. However, most $H_2$-evolving hydrogenases are extremely sensitive to $O_2$, which is an inherent byproduct of cyanobacterial photosynthesis. Therefore, to establish a successful cyanobacterium-bacterium hybrid system using $H_2O$ as the electron donor, one critical requirement is to use a hydrogenase that is not only tolerant to $O_2$ but also catalytically active in the presence of $O_2$.

$O_2$-tolerant hydrogenases with useful rates of $H_2$ production have not been found in nature, and so there is considerable interest in the genetic engineering of such a protein. The present invention addresses these problems.

LITERATURE CITATIONS

Posewitz et al. (2004) J Biol Chem. 279(24):25711-20 describe radical S-adenosylmethionine proteins required for the assembly of an active Fe—Fe hydrogenase. Methods of cell-free protein synthesis are described, for example, in U.S. Pat. No. 6,337,191 B1; U.S. Patent Published Application 20020081660; U.S. Patent Published Application 20040209321; and International Applications WO2004/016778; WO 2005/010155; WO 00/55353; and WO 00/55353, each herein incorporated by reference. U.S. Pat. No. 7,351,563, issued Apr. 1, 2008, discloses method of producing active hydrogenase in a cell-free synthesis system, and is hereby specifically incorporated by reference.

SUMMARY OF THE INVENTION

Compositions and methods are provided for $O_2$-tolerant Fe—Fe hydrogenase. Hydrogenases of interest include Fe—Fe hydrogenases that primarily catalyze $H_2$ evolution, including, without limitation *Clostridium pasteurianum* Fe—Fe hydrogenase (CpI) and derivatives; variants; homologs; and the like, including without limitation those enzymes provided in SEQ ID NO:1-5. The hydrogenases comprise specific amino acid substitutions relative to the native or wild-type (WT) enzymes, which are extremely sensitive to $O_2$. In some embodiments of the invention, polypeptide compositions are provided of $O_2$-tolerant Fe—Fe hydrogenase.

In some embodiments of the invention, the $O_2$ tolerant Fe—Fe hydrogenase is a modified protein of a *Clostridium* species, where specific amino acid changes are introduced to increase the $O_2$ tolerance of the enzyme, for example to provide faster $H_2$ production, higher $O_2$ tolerance, or both.

In some embodiments the $O_2$-tolerant Fe—Fe hydrogenase is CpI, where the native enzyme (with reference to SEQ ID NO:1) is modified by the substitution of one or more amino acids surrounding the Fe—S clusters, including without limitation substitutions at one or more of residues L192, G194; T356 and S357. In some embodiments the amino acid substitutions are one or more of L192G; G194C; T356V and S357T. In some embodiments the amino acid substitution comprises both T356V and S357T. In some embodiments, the amino acid substitutions are selected from the substitutions set forth in Table 2.

In some embodiments the hydrogenase comprises a sequence set forth in any one of SEQ ID NO:2, 3, 4 or 5, modified by introduction of one or more amino acid substitutions set forth in Table 2 in the corresponding residue to that of the CpI protein, e.g. as determined by a BLAST alignment.

In some embodiments, the hydrogenase corresponds to SEQ ID NO:2, which is modified at one or more of residues L191, G193, N355 and D356. In some embodiments the amino acid substitution comprises one or both of L191G; and G193C.

In some embodiments the hydrogenase corresponds to SEQ ID NO:3, which is modified at one or more of residues L192, G194; T356 and A357. In some embodiments the amino acid substitutions are one or more of L192G; G194C; T356V and A357T. In some embodiments the amino acid substitution comprises both T356V and A357T.

In some embodiments the hydrogenase corresponds to SEQ ID NO:4, which is modified at one or more of residues L192, G194; T356 and A357. In some embodiments the amino acid substitutions are one or more of L192G; G194C; T356V and A357T. In some embodiments the amino acid substitution comprises both T356V and A357T.

In some embodiments the hydrogenase corresponds to SEQ ID NO:5, which is modified at one or more of residues L191, G193; N355 and D356. In some embodiments the amino acid substitutions are one or both of L191G; G193C.

In some embodiments, the invention provides isolated nucleic acid molecules including a sequence of nucleotides that encode a modified hydrogenase polypeptide as set forth herein. The nucleic acid molecules may be operably linked to a preselected regulatory sequence, enhancer sequence, silencer sequence, or promoter. The isolated nucleic acids may further be provided in a vector suitable for cell-free polypeptide synthesis, or for cell based expression, including expression in photosynthetic microorganisms.

In some embodiments of the invention a genetically modified organism for generation of $H_2$ is provided, comprising a $O_2$-tolerant Fe—Fe hydrogenase as described herein. In some embodiments a cell-free system for generation of $H_2$ is provided, comprising a $O_2$-tolerant Fe—Fe hydrogenase described herein. The in vitro cell-free system for the generation of $H_2$, or the modified cell for the generation of $H_2$, may further comprise glucose 6-phosphate, ferredoxin-NADP-reductase (FNR); ferredoxin; and NADP. The in vitro cell-free system for the generation of $H_2$, or the modified cell for the generation of $H_2$, may further comprise a physiologically active photosynthetic system, e.g. PSI, PSII or both. The system can provided for $H_2$ generation over a sustained period of time in the presence of $O_2$, e.g. for at least about 15 minutes, at least about 30 minutes, at least about 45 minutes, at least about 1 hour or more. The in vitro cell-free system for the generation of $H_2$, or the modified cell for the generation of $H_2$, may also find use as a screening tool, and as a means of producing $H_2$.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION OF THE EMBODIMENTS

Figure 1:
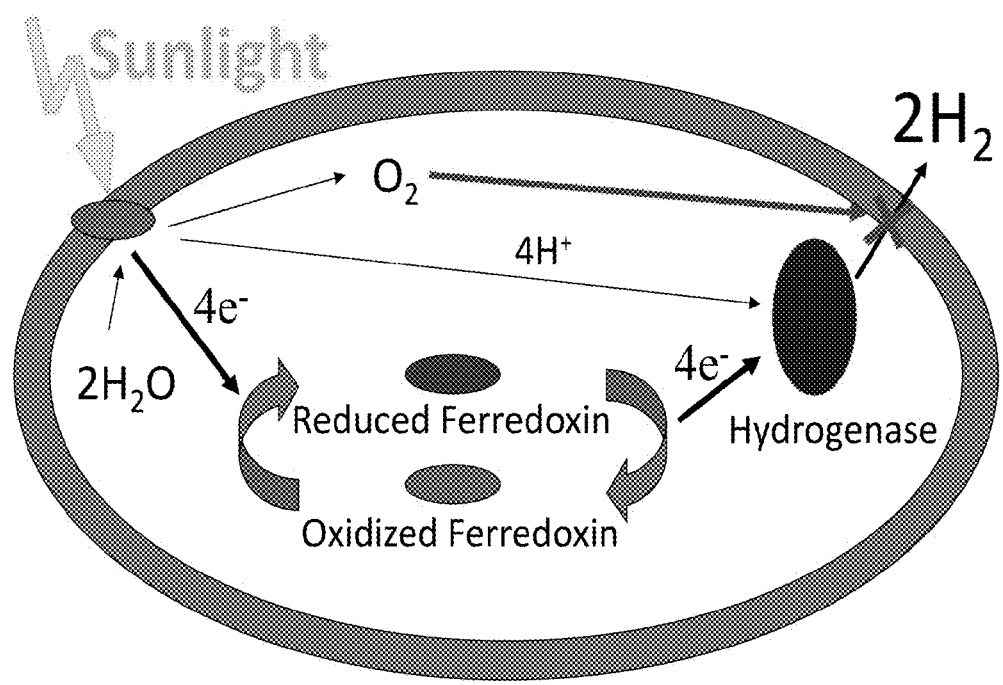
FIG. 1: The general concept of photosynthetic $H_2$ production illustrating one obstacle: $O_2$ inactivation of the hydrogenase.

Specific amino acid positions in hydrogenase have been identified that, when altered from the WT residues, increase $O_2$ tolerance of Fe—Fe hydrogenase.

Throughout this application, various publications, patents, and published patent applications are referred to by an identifying citation. The disclosures of these publications, patents, and published patent specifications referenced in this application are hereby incorporated by reference into the present disclosure to more fully describe the state of the art to which this invention pertains.

The practice of the present invention will employ, unless otherwise indicated, conventional techniques of molecular biology, microbiology, cell biology and recombinant DNA, which are within the skill of the art. See, e.g., Sambrook, Fritsch, and Maniatis, MOLECULAR CLONING: A LABORATORY MANUAL, 2nd edition (1989); CURRENT PROTOCOLS IN MOLECULAR BIOLOGY, (F. M. Ausubel et al. eds., 1987); the series METHODS IN ENZYMOLOGY (Academic Press, Inc.); PCR 2: A PRACTICAL APPROACH (M. J. McPherson, B. D. Hames and G. R. Taylor eds., 1995); and ANIMAL CELL CULTURE (R. I. Freshney. Ed., 1987); "Transgenic Animal Technology: A Laboratory Handbook," by Carl A. Pinkert, (Editor) First Edition, Academic Press; ISBN: 0125571658.

All publications, patents and patent applications cited herein, whether supra or infra, are hereby incorporated by reference in their entirety.

As used in this specification and the appended claims, the singular forms "a," "an" and "the" include plural references unless the content clearly dictates otherwise. Thus, for example, reference to "a polypeptide" includes a mixture of two or more such agents.

Definitions

Hydrogenase. Hydrogenases catalyse the reversible oxidation/production of molecular hydrogen ($H_2$) and play a vital role in anaerobic metabolism. Metal containing hydrogenases are subdivided into three classes: Fe—Fe hydrogenases, Ni—Fe hydrogenases, and Fe hydrogenases. $H_2$ oxidation is coupled to the reduction of electron acceptors such as $O_2$, nitrate, sulphate, $CO_2$ and fumarate, whereas proton reduction ($H_2$ evolution) is coupled to molecules such as ferredoxin. The methods of the invention may be applied to any of the Fe—Fe hydrogenases.

In one embodiment, the term "hydrogenase" as used herein refers to an enzyme that meets one or more of the criteria provided herein. Using these criteria, one of skill in the art can determine the suitability of a candidate enzyme for use in the methods of the invention. Many enzymes will meet multiple criteria, including two, three, four or more of the criteria, and some enzymes will meet all of the criteria.

The terms "hydrogenase" can refer to a full length enzyme or fragment thereof with the capability of catalyzing $H_2$ oxidation/production.

Hydrogenases of the invention include enzymes having at least about 20% sequence identity at the amino acid level, more usually at least about 40% sequence identity, and preferably at least about 70% sequence identity to one of the following hydrogenases: *Chlamydomonas reinhardtii* iron-iron-hydrogenase (Genbank accession AY055756); *Clostridium pasteurianum* hydrogenase (Genbank accession AAA23248.1); *Megasphaera elsdenii* hydrogenase (Genbank accession AF120457); *Desulfovibrio vulgaris* hydrogenase (Genbank accession CAA26266.1). For example, see Forestier et al. (2003) Eur. J. Biochem. 270 (13), 2750-2758; Meyer et al. (1991) Biochemistry 30:9697-9704; Voordouw et al. (1985) Eur. J. Biochem. 148:515-520; Atta et al. (2000) Biochim Biophys Acta. 1476(2):368-71; Fauque et al. (1988) FEMS Microbiol. Rev. 4, 299-344; Cammack et al. (1994) Methods Enzymol. 243, 43-68; and de Lacey et al. (1997) J. Am. Chem. Soc. 119, 7181-7189, each herein incorporated by reference.

Homology-based identification (for example, by a PILEUP sequence analysis) of enzymes can be routinely performed by those of skill in the art upon contemplation of this disclosure to identify those suitable for use in the methods of the present invention. Such enzymes are usually produced in microorganisms, particularly bacteria. Hydrogenases of the invention also include an enzyme belonging to the enzyme classifications EC 1.12.7.2 and EC 1.12.2.1.

The nucleic acid sequences encoding the above hydrogenases may be accessed from public databases as previously cited. Identification of additional hydrogenases is accomplished by conventional screening methods of DNA libraries or biological samples for DNA sequences having a high degree of similarity to known hydrogenase sequences.

Iron-iron hydrogenase. The hydrogenases containing no other metal than Fe and containing an active site H-cluster consisting of a 4Fe-4S subcluster joined by a cysteine residue to a 2Fe-2S cluster are called Fe—Fe hydrogenases (Fe—Fe $H_2$ases). Two families of Fe—Fe $H_2$ases have been described. Cytoplasmic, soluble, monomeric Fe—Fe $H_2$ases are found in strict anaerobes such as *Clostridium pasteurianum* and *Megasphaera elsdenii*. They are extremely sensitive to inactivation by $O_2$ and catalyze both $H_2$ evolution and uptake. Periplasmic, heterodimeric (Fe—Fe) $H_2$ases from *Desulfovibrio* spp., can be purified aerobically but catalyze mainly $H_2$ oxidation.

3-D structures of $H_2$-evolving Fe—Fe $H_2$ase I from *Clostridium pasteurianum* (CpI) and *Desulfovibrio desulfuricans* uptake hydrogenase (DdH) are known. The overall structure of CpI resembles a mushroom consisting of four domains: the large active site domain forms "cap" and three smaller domains form "stem". The "stem" domains bind four Fe—S clusters and are termed FS4A-FS4B, FS4C and FS2. The N-terminal FS2 domain binds a 2Fe-2S cluster and shares the overall fold with plant-type ferredoxins. The FS4A-FS4B domain is adjacent to the active site domain; it contains two 4Fe-4S clusters and has the overall fold similar to that of bacterial type ferredoxins. The FS4C domain is placed between the FS2 and FS4A-FS4B domains and consists of two α-helices linked by a loop that binds a single 4Fe-4S cluster via one His and three Cys residues. The large subunit of DdH lacks FS4C and FS2 clusters and corresponding domains. The small subunit of DdH has an unusual fold consisting of alternating random coil and four α-helices that form a "belt" around the large subunit.

The active site domain of the Fe—Fe $H_2$ases contains an unusual Fe—S cluster termed the H-cluster. H-cluster consists of the 4Fe-4S subcluster bridged via the Cys thiolate to the Fe—Fe (binuclear iron-iron) subcluster. The two Fe—Fe atoms are designated Fe1 and Fe2 (proximal and distal with respect to the 4Fe-4S subcluster) and are ~2.6 Å apart. With the exception of the bridging Cys, the Fe—Fe subcluster is coordinated by non-protein ligands. In CpI, both Fe—Fe atoms are octahedrally coordinated to five CO/CN ligands, three S ligands and one water molecule. Fe1 and Fe2 are bridged by two S atoms and one CO or CN ligand. The two bridging sulphurs themselves are bridged by atom(s) of unknown identity. In DdH, Fe1 and Fe2 are bridged by a small molecule that has been modelled as 1,3-propanedithiol (PDT). Fe1 is octahedrally coordinated while Fe2 has square pyramidal coordination geometry.

In some embodiments of the invention, the Fe—Fe hydrogenase is derived from a *Clostridium* species, for example as shown in the appended sequences of SEQ ID NO:1, 2, 3, 4 and 5. Hydrogenases of interest include, without limitation, those found in the species *Clostridium botulinum; Clostridium tyrobutyricum; Clostridium perfringens; Clostridium butyricum; Clostridium saccharobutylicum; Clostridium novyi; Clostridium pasteurianum; Clostridium acetobutylicum; Clostridium cellulovorans; Clostridium paraputrificum; Clostridium kluyveri* DSM 555; *Clostridium papyrosolvens*, etc. and the related species *Alkaliphilus metalliredigens, Eubacterium acidaminophilum, Anaerocellum thermophilum, Caldicellulosiruptor saccharolyticus* etc.

$O_2$ tolerance. As used herein, the term $O_2$ tolerance refers to the ability of a hydrogenase enzyme to retain $H_2$ production activity in the presence of molecular oxygen. As is known in the art, even trace levels of $O_2$ are sufficient to inactivate known hydrogenases. Enzymes that have been mutated to increase tolerance have at least about 10% activity, at least about 20% activity, at least about 30% activity or more after a solution of the protein is exposed to 0.01 atm $O_2$ for at least about 5 minutes, at least about 15 minutes, at least about 30 minutes, at least about 45 minutes, at least about 1 hour, or more. The enzymes may be more resistant to $O_2$ when the enzyme is present in a microbial host cell (relative to a solution).

Ferredoxin-NADP-reductase (FNR), EC 1.18.1.2, may be obtained from any suitable source, including *E. coli*, Anaebaena sp., and the like, including FNR from photosynthetic organisms such as higher plants, e.g. *Spinacea oleracea* (spinach).

In photosynthetic organisms, FNR is the last enzyme in the transfer of electrons during photosynthesis from photosystem I to NADPH. In such organisms it is a soluble protein that is found both free in the chloroplast stroma and bound to the thylakoid membrane. This binding occurs opposite to the active site of the enzyme and does not seem to affect the structure of the active site or have a significant impact on the enzyme's activity. In the plant-like family of FNRs, selective evolutionary pressure has led to differences in the catalytic rate enhancements of FNRs in photosynthetic and non-photosynthetic organisms. Electron transfer by FNR is a rate limiting step in photosynthesis, so the plastidic FNRs in plants have evolved to catalyze higher electron transfer rates. These plastidic FNRs are 20-100 fold more active than bacterial FNRs.

In non-photosynthetic organisms, the FNR primarily works in reverse to provide reduced ferredoxin for various metabolic pathways. These pathways include $N_2$ fixation, terpenoid biosynthesis, steroid metabolism, oxidative stress response, and Fe—S protein biogenesis.

For the purposes of the present invention, an active fragment of FNR, i.e. a fragment that confers substantially all of the enzymatic activity of the native protein, e.g. at least about 50% of the activity, at least about 75%, at least about 80%, at least about 90%, at least about 95%, when measured under standard conditions, may be included in a cell or cell-free system for generation of $H_2$.

Ferredoxin. Ferredoxins of interest include, without limitation, *Clostridium pasteurianum* ferredoxin; *Synechocystis* ferredoxin, *E. coli* ferredoxin, *Spinacia oleracea* ferredoxin; *Anabaena* ferredoxin, derivatives; variants; homologs; mutants; and the like. Included, without limitation, are 2Fe-2S, and 4Fe-4S ferredoxins. A candidate ferredoxin may be assayed for $H_2$ production with a hydrogenase and/or FNR of interest, and may be evolved to increase electron transfer rates within such pathways. The ferredoxin may be synthesized in a cell with the hydrogenase.

Sugar. As used herein, the term refers to a number of carbohydrates, such as monosaccharides, disaccharides, oligosaccharides, and polysaccharides, usually pentose or hexose sugars or polymers thereof. Monosaccharides that find use include, without limitation, fructose, arabinose, lyxose, ribose, xylose, ribulose, xylulose, deoxyribose, allose, altrose, glucose, mannose, gulose, idose, galactose, talose. Disaccharides may include sucrose, lactose, maltose, etc. Polysaccharides may include starches, glycogen, cellulose, pectin, peptidoglycan, lipopolysaccharides, capsules, exopolysaccharides, and the like. Sugars may be phosphorylated, e.g. glucose-6-phosphate, etc. Sugars may be included in the reaction mix at a concentration sufficient to provide energy for $H_2$ evolution, e.g. from about 1 mM to about 1000 mM, and may be about 5 mM, 10 mM, 25 mM, 50 mM, 75 mM, 100 mM, 250 mM, 500 mM, 750 mM, 1000 mM, and may also be supplied by continuous addition.

Cell-free reaction mix: as used herein refers to a reaction mixture comprising an $O_2$ tolerant hydrogenase as described herein, and such components as are required for the generation of $H_2$. The hydrogenase may be capable of catalyzing the synthesis of $H_2$ from sugar, which sugar may be a phosphorylated or non-phosphorylated sugar. A reaction mixture of interest comprises extracts from bacterial cells, and the synthesis is performed under conditions in which some $O_2$ may be present, e.g. up to about 1 vol. % $O_2$ in the reaction headspace; up to about 2 vol. % $O_2$, up to about 3 vol. % $O_2$, up to about 4 vol. % $O_2$, up to about 5 vol. % $O_2$, or more.

The volume percent of cell extract in the reaction mix will vary, where the extract is usually at least about 10% of the total volume; more usually at least about 20%; and in some instances may provide for additional benefit when provided at least about 50%; at least about 60%; or at least 75% of the total volume. In certain industrial applications the volume percent of extract may be around about 90% or higher.

The reaction mixture may be further supplemented with one or more of niacin, nicotinamide, NAD, etc., usually at a concentration of from about 0.1 mM to 10 mM, e.g. at about 0.5 mM, about 1.0 mM, about 4 mM, etc. as a precursor or source of NAD and NADP; a nuclease, particularly a ribonuclease, which may be used at a conventional dose for example from about 0.5 □g/ml to about 50 □g/ml or higher, to break down nucleic acids and generate adenine; and an agent to inactivate the endogenous microbial cell glycolytic pathway and thus maximize conversion yields.

The terms "nucleic acid molecule" and "polynucleotide" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers.

A "coding sequence" or a sequence which "encodes" a selected polypeptide, is a nucleic acid molecule which is transcribed (in the case of DNA) and translated (in the case of mRNA) into a polypeptide, for example, in a cell-free polypeptide synthesis reaction; or in vivo when placed under the control of appropriate regulatory sequences (or "control elements"). The boundaries of the coding sequence are typically determined by a start codon at the 5' (amino) terminus and a translation stop codon at the 3' (carboxy) terminus. A transcription termination sequence may be located 3' to the coding sequence. Other "control elements" may also be associated with a coding sequence.

"Operably linked" refers to an arrangement of elements wherein the components so described are configured so as to perform their usual function. Thus, a given promoter that is operably linked to a coding sequence (e.g., a reporter expression cassette) is capable of effecting the expression of the coding sequence when the proper enzymes are present. The promoter or other control elements need not be contiguous with the coding sequence, so long as they function to direct the expression thereof. For example, intervening un-translated yet transcribed sequences can be present between the promoter sequence and the coding sequence and the promoter sequence can still be considered "operably linked" to the coding sequence.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning and expression vehicles, as well as integrating vectors.

"Purified polynucleotide" refers to a polynucleotide of interest or fragment thereof which is essentially free, e.g., contains less than about 50%, preferably less than about 70%, and more preferably less than about 90%, of the protein with which the polynucleotide is naturally associated. Techniques for purifying polynucleotides of interest are well-known in the art and include, for example, disruption of the cell containing the polynucleotide with a chaotropic agent and separation of the polynucleotide(s) and proteins by ion-exchange chromatography, affinity chromatography and sedimentation according to density.

A "polypeptide" is used in it broadest sense to refer to a compound of two or more subunit amino acids, amino acid analogs, or other peptidomimetics. The subunits may be linked by peptide bonds or by other bonds, for example ester, ether, etc. As used herein, the term "amino acid" refers to either natural and/or unnatural or synthetic amino acids, including glycine and both the D or L optical isomers, and amino acid analogs and peptidomimetics.

Before describing the present invention in detail, it is to be understood that this invention is not limited to particular formulations or method parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

Modified Hydrogenase Polypeptides

Modified hydrogenase polypeptides are provided, which modifications provide for increased $O_2$ tolerance in the active protein, as described above. The amino acid substitutions may also be combined with other amino acid substitutions that enhance, or that do not adversely affect the $H_2$ production activity. The modified hydrogenase polypeptides have a tolerance to $O_2$ for at least about 2.5 minutes, at least about 5 minutes, at least about 7.5 minutes, at least about 10 minutes, or more. The specific activity after exposure to $O_2$ may be, relative to the activity in the absence of $O_2$, at least about 20% of the specific activity, at least about 30%, at least about 40%, at least about 50% or more, following exposure to 0.01 atm. $O_2$ for 5 minutes.

In addition to the above modifications, the sequence of hydrogenase polypeptides may be altered in various ways known in the art to generate targeted changes in sequence. The sequence changes may be substitutions, insertions or deletions, e.g. truncations at the amino or carboxy terminus. Such alterations may be used to alter properties of the protein, by affecting the stability, specificity, etc. Techniques for in vitro mutagenesis of cloned genes are known. Examples of protocols for scanning mutations may be found in Gustin et al., Biotechniques 14:22 (1993); Barany, Gene 37:111-23 (1985); Colicelli et al., Mol Gen Genet 199:537-9 (1985); and Prentki et al., Gene 29:303-13 (1984). Methods for site specific mutagenesis can be found in Sambrook et al., Molecular Cloning: A Laboratory Manual, CSH Press 1989, pp. 15.3-15.108; Weiner et al., Gene 126:35-41 (1993); Sayers et al., Biotechniques 13:592-6 (1992); Jones and Wnistorfer, Biotechniques 12:528-30 (1992); Barton et al., Nucleic Acids Res 18:7349-55 (1990); Marotti and Tomich, Gene Anal Tech 6:67-70 (1989); and Zhu Anal Biochem 177:120-4 (1989). In addition, such techniques as "QuikChange" (Invitrogen) can be employed or targeted mutations can be introduced by total or partial synthesis of the gene from chemically synthesized oligonucleotides by overlap extension PCR techniques.

The peptides may be joined to a wide variety of other oligopeptides or proteins for a variety of purposes. By providing for expression of the subject peptides, various post-expression modifications may be achieved. For example, by employing the appropriate coding sequences, one may provide farnesylation or prenylation. The peptides may also be combined with other proteins; with ligands or receptors of interest; with viral proteins, transmembrane localization sequences etc., or with specific binding agents including other polypeptides.

The hydrogenase of the invention may be produced in eukaryotic or prokaryotic cells, may be synthesized in vitro, or synthesized in a cell free synthetic system. Expression in photosynthetic cells is of particular interest, e.g. plants cells, photosynthetic microorganisms, and the like.

Modifications of interest that do not alter primary sequence include chemical derivatization of polypeptides, e.g., acetylation, amidation, carboxylation, etc. Also embraced are sequences that have phosphorylated amino acid residues, e.g. phosphotyrosine, phosphoserine, or phosphothreonine.

Also included in the subject invention are peptides that have been modified using ordinary molecular biological techniques and synthetic chemistry so as to improve their resistance to proteolytic degradation or to optimize solubility properties or to render them more suitable as a catalyst. Analogs of such polypeptides include those containing residues other than naturally occurring L-amino acids, e.g. D-amino acids or non-naturally occurring synthetic amino acids. D-amino acids may be substituted for some or all of the amino acid residues.

The subject peptides may be prepared by cell-free synthesis, using conventional methods as known in the art. Cell-free synthesis of polypeptides utilizes a reaction mix comprising biological extracts and/or defined reagents. The reaction mix will comprise a template for production of the macromolecule, e.g. DNA, mRNA, etc.; monomers for the macromolecule to be synthesized, e.g. amino acids, nucleotides, etc., and such co-factors, enzymes and other reagents that are necessary for the synthesis and activation, e.g. ribosomes, tRNA, polymerases, transcriptional factors, maturases, etc. For example, a cell-free system may be used as described in U.S. Pat. No. 7,351,563 using a cell-extract containing 3 maturases expressed from genes obtained from *Shewanella oneidensis*. Such synthetic reaction systems are well-known in the art, and have been described in the literature. The cell free synthesis reaction may be performed as batch, continuous flow, or semi-continuous flow, as known in the art.

The polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, these compositions will comprise at least 20% by weight of the desired product, more usually at least about 75% by weight, and preferably at least about 95% by weight, in relation to contaminants related to the method of preparation of the product and its purification. Usually, the percentages will be based upon total protein.

In one embodiment of the invention, the hydrogenase consists essentially of a polypeptide sequence of at least 100 amino acids, at least 200, amino acids, at least 300 amino acids, at least 400 amino acids, up to the full length of any of SEQ ID NO:1-5 and further comprising at least one amino acid substitution as described herein. By "consisting essentially of" in the context of a polypeptide described herein, it is meant that the polypeptide is composed of the hydrogenase sequence, which sequence may be flanked by one or more amino acid or other residues that do not materially affect the basic characteristic(s) of the polypeptide. Also included are fusions of this sequence with a binding partner of interest.

Amino acid substitutions (numbering relative to SEQ ID NO:1) that provide for faster $H_2$ production include A156C, G158C, M166C, L192C, Q195C, G185C+I197C, N160C+L192C, T163C+Y164C, Y164C+I197C, A165C+L191C, L192E, L192G, P301C, T356C, M498C, N505C+P301C, N505C, T356C+S357C, S357A, S357V, S357I, S357P, T356V+S357T. One or more of these substitutions may be combined with amino acid substitutions that provide for greater $O_2$ tolerance.

Amino acid substitutions (numbering relative to SEQ ID NO:1) that provide for greater $O_2$ tolerance include A156C, M166C, G194C, Q195C, I197C, A156C+L191C, G158C+I197C, N160C+T161C, N160C+A165C, N160C+L192C, N160C+Q195C, N160C+I197C, T161C+G194C, T161C+I197C, T163C+N189C, T163C+Q195C, T163C+I197C, Y164C+Q195C, A165C+N189C, A165C+L192C, A165C+Q195C, A165C+I197C, M166C+Q195C, M166C+I197C, F185C+I197C, N189C+G194C, N189C+I197C, L191C+L192C, L191C+I197C, Q195C+I197C, L192F, L192W, L192S, L192D, L192G, P301C, T356C, S357C, P301C+T356C, P301C+A498C, P301C+G502C, G302C+T356C, G302C+S357C, G302C+A498C, W303C+G507C, P354C+G508C, T356C+S357C, S357C+A498C, S357C+N505C, T356V, T356I, T356L, T356P, S357A, S357V, S357I, S357L, S357T, S357P, T356V S357T, T356V+S357V, T356V+S357P.

The invention includes nucleic acids encoding the peptides of the invention. Hydrogenase coding sequences can be generated by methods known in the art, e.g. by in vitro synthesis, recombinant methods, etc. to provide a coding sequence that corresponds to a hydrogenase polypeptide that can serve as an intermediate in the production of the hydrogenase peptide. Using the known genetic code, one can produce a suitable coding sequence. Double or single stranded fragments can be obtained from the DNA sequence by chemically synthesizing oligonucleotides in accordance with conventional methods, by restriction enzyme digestion, by PCR amplification, etc.

Hydrogenase encoding nucleic acids can be provided as a linear molecule or within a circular molecule, and can be provided within autonomously replicating molecules (vectors) or within molecules without replication sequences. Expression of the nucleic acids can be regulated by their own or by other regulatory sequences known in the art. The nucleic acids can be introduced into suitable host cells using a variety of techniques available in the art, such as by conjugation, transfection with naked or encapsulated nucleic acids, liposome-mediated DNA transfer, intracellular transportation of DNA-coated latex beads, protoplast fusion, viral infection, electroporation, gene gun, calcium phosphate-mediated transfection, and the like.

Expression vectors may be used to introduce a hydrogenase coding sequence into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least about several days to several weeks.

Methods of transferring genetic material into bacterial cells are well known in the art, including transfection, e.g. by $Ca^{++}$, electroporation, etc.; infection with viral vectors; conjugative mating, etc. Any of these methods may be used as appropriate for the desired host cell.

For example, genes and transposons are routinely transferred to organisms such as filamentous cyanobacteria by conjugal transfer of plasmids from *Escherichia coli* or another suitable host. Suitable methods for such transfer are described, for example, by Elhai and Wolk P (1988) Methods in Enzymology. 167: 747-754; and Elhai et al. (1997) J Bacteriol 179:1998-2005, each herein incorporated by reference.

The expression cassettes of the present invention may be introduced into the genome of plant or microorganism, including, for example, photosynthetic microorganisms in order to produce transgenic microorganisms and plants for purposes of $H_2$ production methods of the present invention. A variety of transformation techniques are well known in the art. Those methods include, but are not limited to, direct microinjection into nuclei, electroporation; calcium phosphate precipitation, liposomes, protoplast fusion, viral infection, and the like.

The amount of protein produced in a translation reaction can be measured in various fashions. One method relies on the availability of an assay that measures the activity of the particular protein being translated. Examples of assays for measuring protein activity are the methyl viologen assay described in the examples. These assays measure the amount of functionally active protein produced from the translation reaction. Activity assays will not measure full length protein that is inactive due to improper protein folding or lack of other post translational modifications necessary for protein activity.

An alternative assay for the hydrogenase activity is one that demonstrates actual evolution of $H_2$, as many useful applications of hydrogenase synthesis require the production of $H_2$. To produce $H_2$, a reaction must contain a source of electrons, a source of protons, active hydrogenase protein, and an electron carrier that can deliver electrons to hydrogenase. The electron source may be provided as a reduced carrier, e.g. reduced methyl viologen; reduced ferrodoxin; etc. A suitable buffering agent may serve as a source of protons. The candidate synthesis product serves as a source of hydrogenase. $H_2$ is evolved as electrons are donated from the reduced carrier to hydrogenase. Where the carrier provides for a colorimetric change, such as with methyl viologen, the results may be read spectrophotometrically. Alternatively, gas chromatography or other methods may be used to detect the presence of $H_2$ evolved from the reaction.

In addition, the invention includes kits comprising the polypeptides, nucleic acids, and vectors described herein. The kits can also include a substrate, and instructions for use in methods described herein.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Methods recited herein may be carried out in any order of the recited events which is logically possible, as well as the recited order of events.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Experimental

Figure 2:
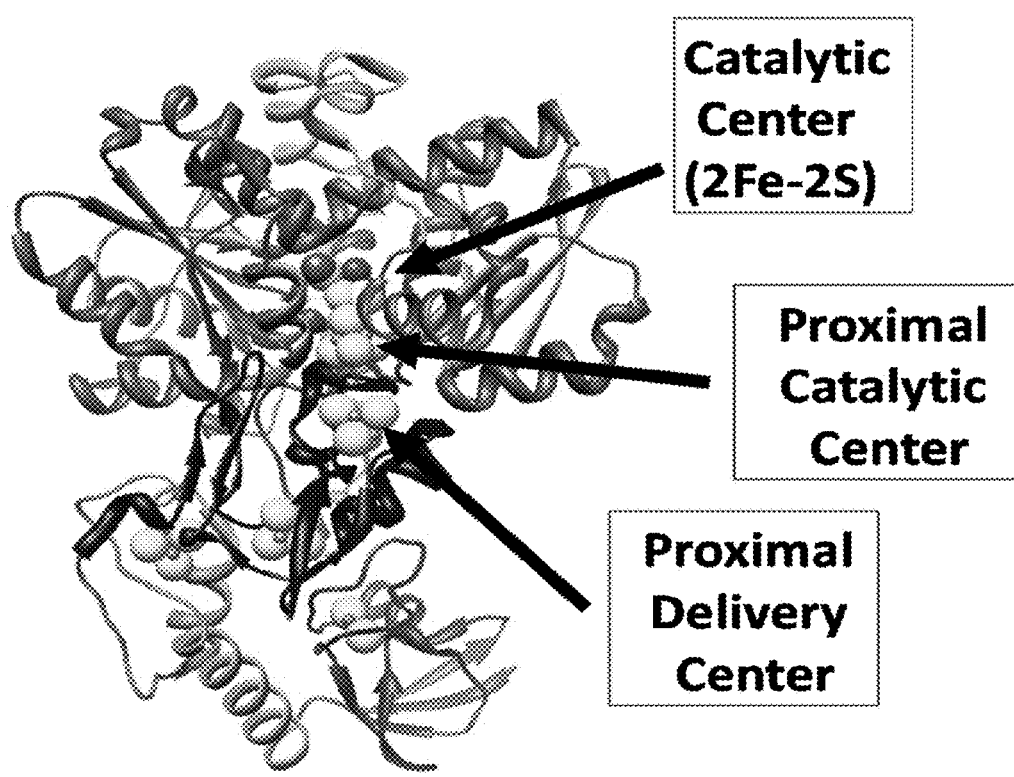
FIG. 2: CpI published structure with key Fe—S clusters labeled.

FIG. 1 illustrates a long term objective to engineer a photosynthetic bacterium to efficiently produce $H_2$ from sunlight and water. The solar energy activates the photosystem to split water and a new pathway uses a small protein, ferredoxin, to direct the electrons to a prolific $H_2$-producing enzyme, an Fe—Fe hydrogenase. The first technical barrier was that the hydrogenase was rapidly inactivated by $O_2$, a side product of water splitting. However, recent progress has been made toward reengineering the Fe—Fe hydrogenase, CpI, to be $O_2$-tolerant by mutating residues near the proximal catalytic and/or proximal delivery Fe—S clusters (FIG. 2)

The more complex type of Fe—Fe hydrogenases has a complex H-cluster active site composed of a catalytic 2Fe-2S cluster with additional adducts. A neighboring 4Fe-4s cluster, bridged by a cysteinyl thiol, directly supplies the electrons required to reduce protons to then form $H_2$. This adjacent cluster is referred to herein as the proximal catalytic cluster (PCC). These electrons are supplied from a ferredoxin protein by way of an electron conduction pathway within the enzyme composed of three 4Fe-4S clusters and one 2Fe-2S cluster. The conduction cluster nearest the proximal catalytic cluster supplies the electrons into the enzyme's active site. This conduction cluster is referred to herein as the proximal delivery cluster (PDC). $O_2$ tolerance of the enzyme is improved by substituting residues close to the Fe or S atoms of either the PDC or PCC.

Figure 3:
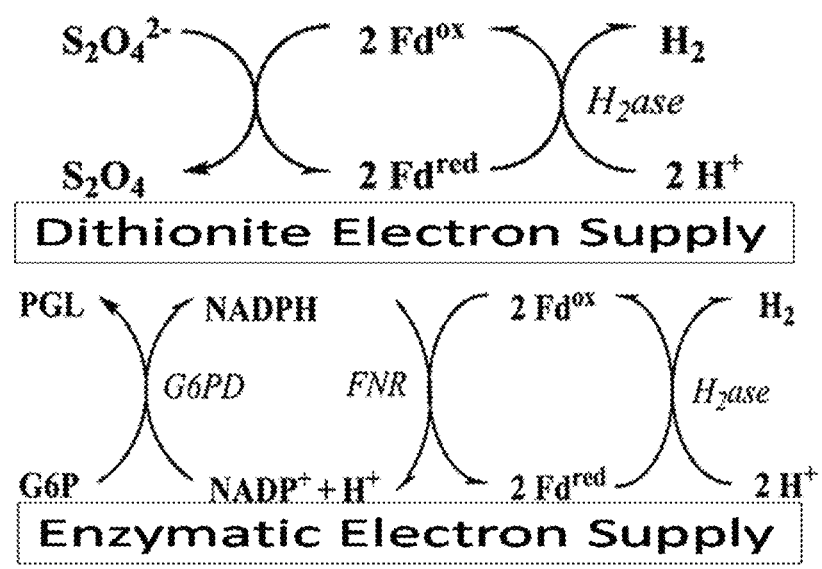
FIG. 3: Two reaction series used for evaluating $O_2$ sensitivity of the hydrogenases during $H_2$ production (PGL=phosphogluconolactone, G6P=glucose 6-phosphate, G6PD=glucose 6-phosphate dehydrogenase, FNR=ferredoxin NADP reductase, and Fd=ferredoxin)

To facilitate a search for the desired $O_2$ tolerance (during $H_2$ production), we developed two types of reaction series (FIG. 3). The top one uses a strong reducing agent, dithionite, to reduce ferredoxin (Fd) as the source of electrons for the hydrogenase ($H_2$ase). This reaction is not compatible with $O_2$ presence because dithionite rapidly reduces $O_2$ to water. However, it is useful for determining residual activity after long $O_2$ exposures. The bottom reaction uses a more natural electron source, Glucose 6-phosphate (G6P). G6P dehydrogenase (G6PD) transfers two electrons from G6P to reduce $NADP^+$, and Ferredoxin $NADP^+$ Reductase (FNR) then transfers the electrons to Fd so they can be accepted by the $H_2$ase.

Developing $O_2$ tolerance by directed mutation. FIG. 2 shows the structure of CpI. The yellow spheres are sulfur atoms and the smaller red and blue spheres indicate the CO and CN adducts on the catalytic 2Fe-2S cluster. The adjacent 4Fe-4S cluster is labeled as the proximal catalytic center, and the next one, that directly provides electrons to the H-cluster, we call the proximal delivery center. In our first CpI screen using the $H_2$ oxidation assay, the mutations most influential for increasing $O_2$ tolerance were located adjacent to the proximal delivery center. However, these changes only increased $O_2$ tolerance when the enzyme was consuming $H_2$ and did not confer $O_2$ tolerance during $H_2$ production. More recently, work by others with a Ni—Fe hydrogenase that primarily consumes $H_2$ indicated that two extra Cys residues surrounding the Fe—S center nearest the enzyme's active site were required for $O_2$ tolerance. Such cysteines are not present in the Fe—Fe hydrogenases; and motivated by the Ni—Fe hydrogenase structure, we have been evaluating the introduction of Cys and non-Cys near the proximal delivery and catalytic clusters in CpI.

Figure 4:
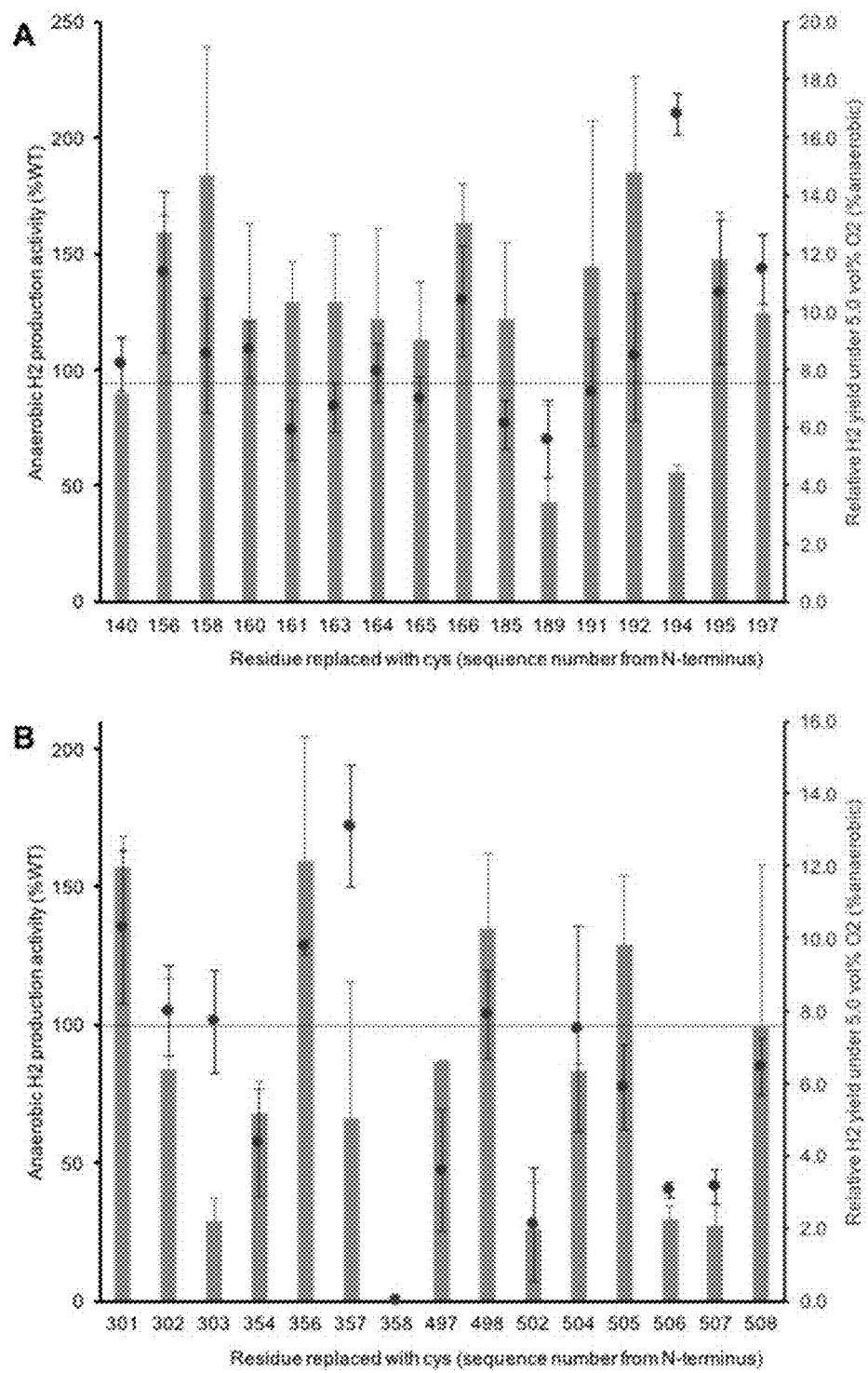
FIG. 4: $H_2$ production activity and $O_2$ tolerance of CpI mutants with single Cys replacements near the (A) Proximal Delivery Center (PDC) or (B) the Proximal Catalytic Center (PCC). The dotted line represents the aerobic $H_2$ yield by the WT CpI (7.5% of the anaerobic yield over the same time period).
Figure 5:
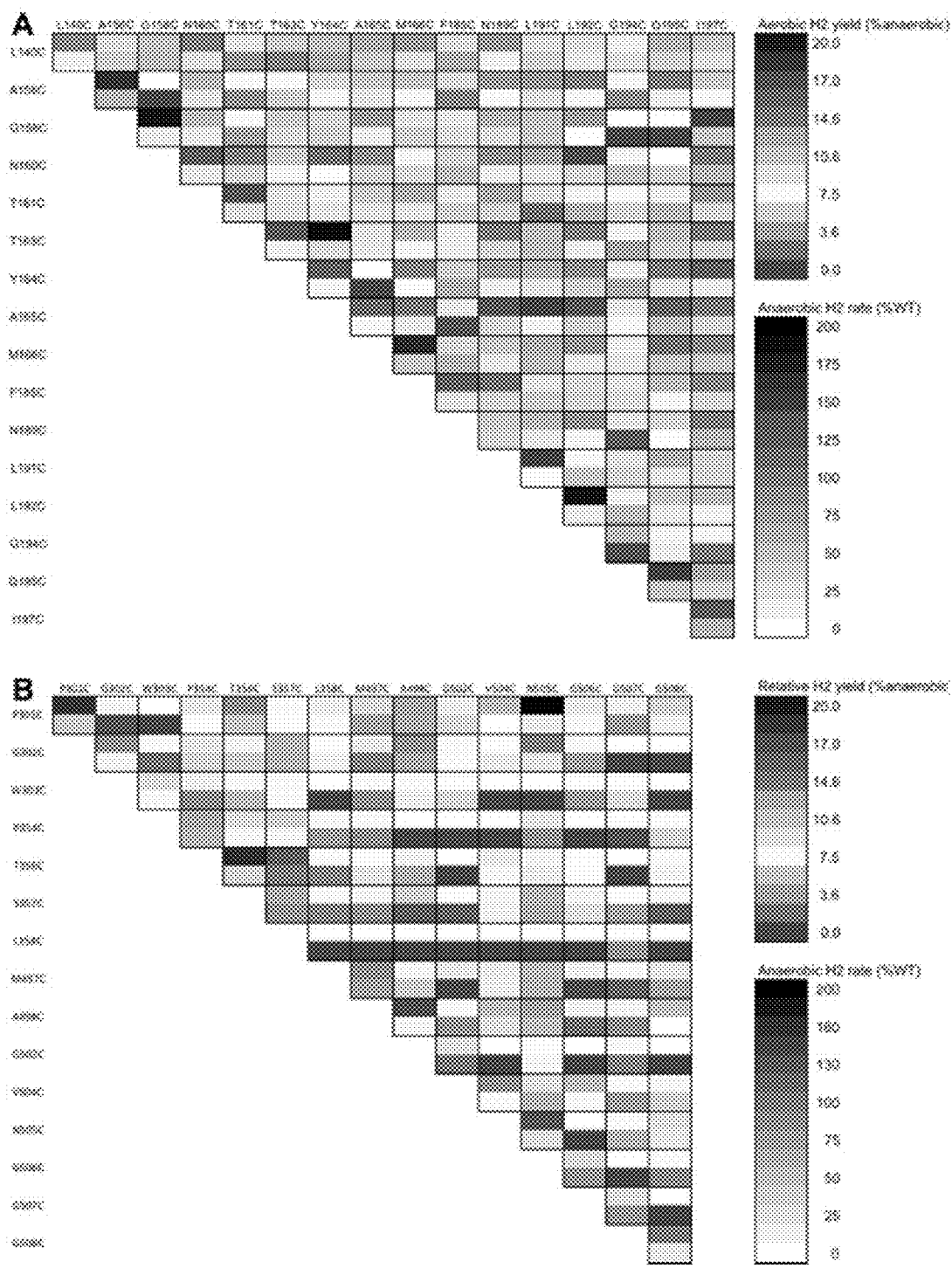
FIG. 5: $H_2$ production activity and $O_2$ tolerance of CpI mutants with double Cys replacements near the (A) PDC or (B) PCC. The upper and lower tile for each mutant represent the anaerobic $H_2$ production activity and the aerobic $H_2$ yield, respectively.
Figure 6:
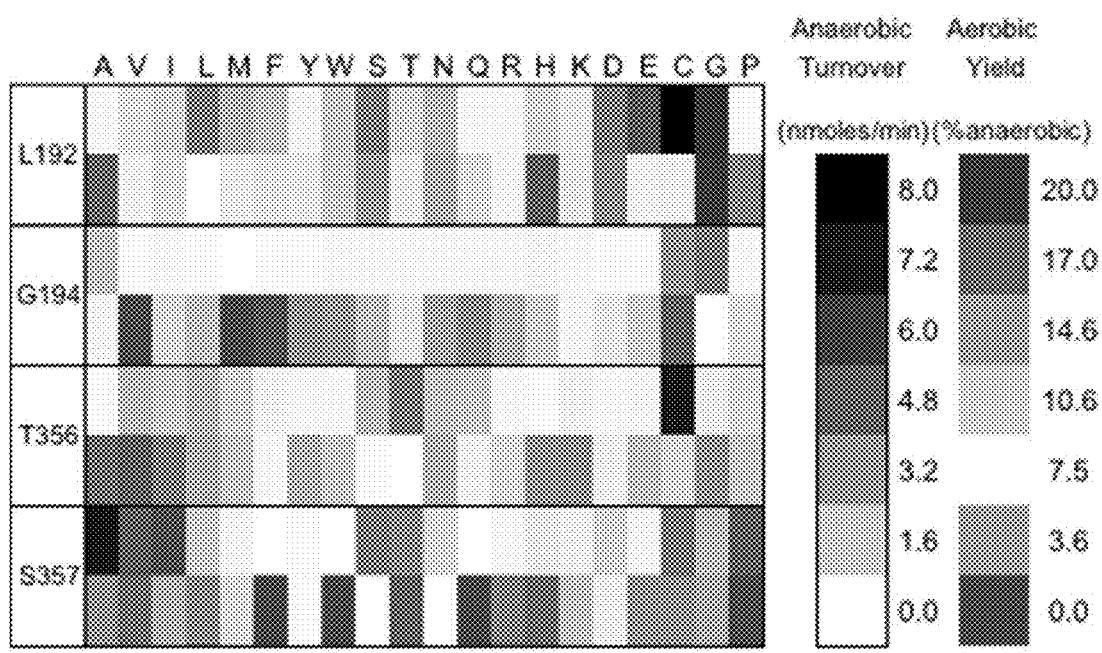
FIG. 6: $H_2$ production activity and $O_2$ tolerance of CpI saturation mutagenesis library at 4 selected sites. The upper and lower tile for each mutant represent the anaerobic $H_2$ production activity and the aerobic $H_2$ yield, respectively.
Figure 7:
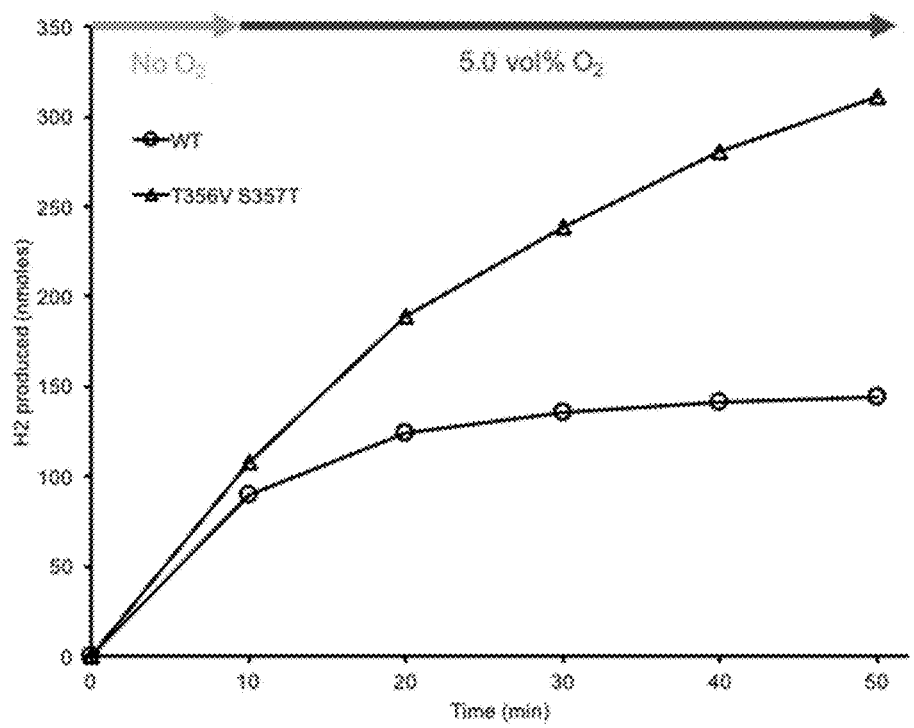
FIG. 7: Double amino acid replacement of T356V S357T confers higher $O_2$ tolerance during NADPH-driven $H_2$ production.

We first replaced all residues within 6.5 Å of the PDC or PCC with Cys to see which sites have high influence on the anaerobic $H_2$ production activity and aerobic $H_2$ yield. We then combined single Cys replacements around each cluster to create CpI mutants with double Cys replacements. We did not discover any double cysteine replacement mutants that showed a higher aerobic yield, i.e. $O_2$ tolerance, than the best single Cys replacement mutant, $CpI^{G194C}$ (FIGS. 4 and 5; all amino acid residue locations referred to in this section are based on SEQ ID NO: 1). However, we did see a few combinations that resulted in higher $O_2$ tolerance than the improvement from either of the individual Cys replacements that were combined. Next, we selected two sites around each proximal cluster that showed the highest improvement in the anaerobic $H_2$ production activity or $O_2$ tolerance, and saturation mutagenesis libraries were created for these 4 sites. When evaluating these libraries, we observed non-Cys replacements, e.g., L192G that improved $O_2$ tolerance more than the highest level obtained with Cys replacements (FIG. 6). Furthermore, several combinations of non-Cys replacements at T356 and S357 synergistically improved $O_2$ tolerance. These two sites had previously shown synergistic enhancement in $O_2$ tolerance of CpI when replaced with Cys. The most promising mutant from our library was identified with T356V and S357T substitutions. FIG. 7 compares the WT CpI to this mutant using the NADPH-driven $H_2$ production reaction series (FIG. 3). The first 10 minutes indicated baseline activities, and 5% $O_2$ (chosen to mimic expected production conditions) was then introduced. The mutant retains about 12 times more activity after nearly an hour of $O_2$ exposure. This is by far the most $O_2$ tolerant Fe—Fe hydrogenase ever observed.

It is important to recognize that these mutations are highly non-obvious relative to recognized and suggested mechanisms for oxygen tolerance in hydrogenases. The best studied oxygen tolerance example is for the [NiFe] hydrogenase from *Ralstonia eutropha*. This hydrogenase has been shown to be oxygen tolerant because of two extra cysteines around the iron sulfur center near the catalytic center. This unique center therefore has six cysteines that either help to comprise or that surround the Fe—S center. These extra cysteines serve as an additional reservoir for electrons to allow oxygen molecules that adsorb to the active site to be completely reduced to water. Removing these cysteines causes oxygen sensitivity. Another theory is that oxygen diffusion channels within the protein structure allow the oxygen to reach the active site of [FeFe] hydrogenase, and that closing these channels would increase oxygen tolerance. It is clear that a single cysteine replacement mutants would not be capable of providing either advantage, and further that the combined T356V and S357T substitutions could contribute to neither of the recognized mechanisms. Therefore, the oxygen tolerance observed with the present invention could not have been predicted based on prior observations and the data presented herein demonstrates that oxygen tolerance for [FeFe] hydrogenases is obtained by a new and unpredicted mechanism.

Developing tools for measuring light-dependent electron flux: In photosynthetic organisms, the PSII complex first splits water to produce electrons, protons, and $O_2$. The electrons are then delivered to PSI (using several electron carriers including the protein, plastocyanin) where another photon boosts their energetic content. These electrons are then typically transferred to a native ferredoxin which then selectively delivers the electrons to FNR in order to provide reducing equivalents in the form of NADPH to drive carbon fixation, biosynthesis, and other essential metabolic processes.

Figure 8:
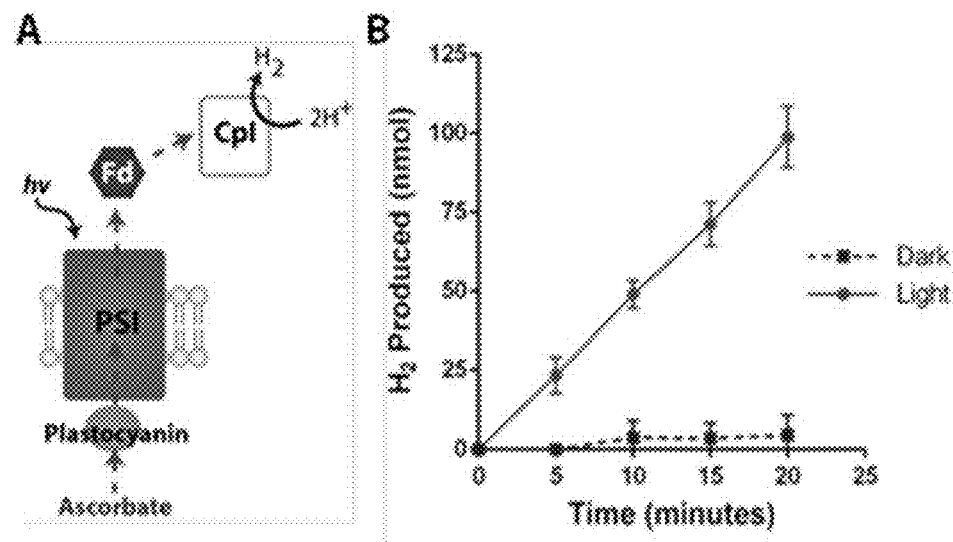
FIG. 8: (A) Electron pathway for PSI-mediated, light dependent $H_2$ production, (B) Early results showing light dependent $H_2$ production.

A goal is to use most of the available reducing equivalents for producing $H_2$ while channeling only those required for cell viability to the FNR. In order to study this more carefully, we have been developing in vitro protocols for light dependent electron flux measurements. Following the lead of Kubota et al., we attached purification tags to PSI subunit proteins in the photosynthetic bacterium, *Synechocystis* sp. PCC 6803. This enabled PSI isolation from cell extracts. In parallel, plastocyanin was also purified. These were combined with the *Synechocystis* ferredoxin and CpI to produce the system diagrammed in FIG. 8A. Ascorbic acid is the initial electron source, but light energy is required to boost the energy level to that needed for ferredoxin reduction and $H_2$ production (FIG. 8B)

Figure 9:
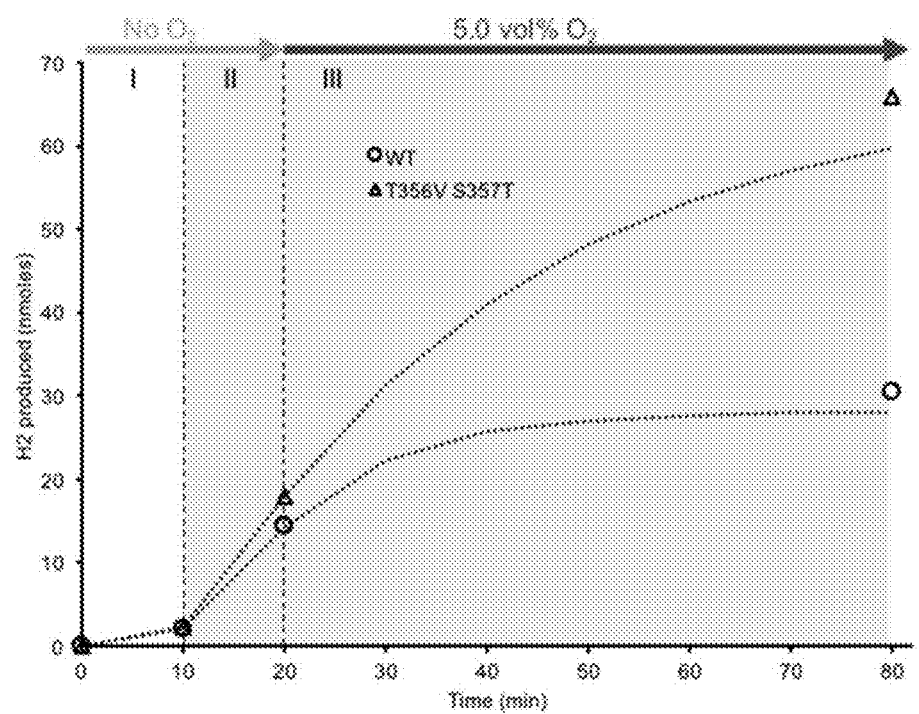
FIG. 9: PSI-mediated, light dependent $H_2$ production with the WT CpI versus the T356V S357T mutant in the presence of 5% $O_2$.

Test with $O_2$-tolerant Fe—Fe hydrogenase. Finally we evaluated the $O_2$ tolerant Fe—Fe hydrogenase in the light-driven, PSI-mediated reaction series (FIG. 9). It was compared to the WT CpI by expressing and maturing both the WT and the mutant in vivo and then purifying the hydrogenases. Under 5.0 vol % $O_2$, $CpI^{T356V\ S357T}$ produced $H_2$ that is equivalent to 70% of the amount expected anaerobically. This is very promising and suggests that light driven $H_2$ production catalyzed by the mutated CpI could continue for several hours in the presence of $O_2$.

The mutation sites within CpI replaced with Cys were chosen based on the distance to the closest Fe or S atom of the proximal 4Fe-4S clusters. The cutoff distance was 6.5 angstrom and we used a software called Chimera in calculating the distance for each site. 17 sites were identified in vicinity of the PDC, and 18 around the PCC. 4 were within the cutoff distance to both proximal clusters.

The genes for these 31 single Cys replacement mutants were created by using a site-directed mutagenesis protocol called QuikChange. A plasmid from our group called pK7 sCpI that contains the gene for CpI WT was used as the DNA template. Once the plasmids for single Cys replacement mutants were obtained, the same protocol was repeated with these plasmids as the template in creating genes for double Cys replacement mutants.

In expressing the mutants, the cell-free protein synthesis technique was first used that had been previously developed. 350 ng of the mutated pK7 sCpI plasmid was mixed in 20 uL of the cell-free (CF) reaction mixture and incubated overnight inside an anaerobic glovebox. 50-200 ug/mL of mutant proteins were obtained in the cell-free buffer after 12-16 hours. As explained before, the most promising mutant, $CpI^{T356V\ S357T}$ and 7 other variants were also expressed and matured in vivo and then purified using a C-terminal strep tag for the more thorough analysis shown in FIGS. 7 and 9.

$O_2$ tolerance of these mutant proteins was first evaluated in the following manner. $H_2$ production reaction mixtures were prepared inside an anaerobic glovebox with an atmosphere of 100% $N_2$. The final concentrations of each reagent (unless otherwise stated) was added in the following order: 50 mM Tris-HCl pH 7.0, 10 mM G6P, 1.0 U G6PD, 5 mM NADPH, 50 μM RrFNR (rice root FNA), 5 μM SynFd (*Synechocystis* ferredoxin). 10 μL of the cell-free reaction product solution that contained CpI mutant proteins was added last. The total reaction volume was 200 μL which was placed at the bottom of 2.0 mL target screw thread vials. Before sealing the vials with rubber septa, magnetic stir bars were put to enable mixing during $O_2$ exposure. After sealing, the samples were removed from the glovebox. The $H_2$ production reactions were incubated at room temperature while mixing at 250 rpm. A 23-gauge needle syringe was used to sample 200 μL of the headspace to measure $H_2$ and $O_2$ concentrations using gas chromatography with a Hewlett Packard 6890 Gas Chromatograph and a ShinCarbon ST 100/120 mesh column. 5.0 vol % $O_2$ was introduced to the headspace of vials by injecting 0.56 mL of air (21% $O_2$) and removing the same volume afterwards. All experiments were done in duplicate and error bars in the figures represent standard deviation.

Aerobic $H_2$ production by the WT and mutant CpI proteins in the light-driven, PSI-mediated reaction series was conducted similarly with the following two differences. First, the reaction mixture contained the following reagents instead: 20 mM ascorbate, 5 μM DCIP, 250 μg/mL plastocyanin, 50 μg/mL PSI, 2 μM SynFd, 100 nM RrFNR, 100 nM CpI (expressed in vivo, maturated and purified), 1 mM NADPH in 50 mM HEPES buffer pH 7.0 with 1 M sucrose, 5 mM $CaCl_2$ & $MgCl_2$. Second, the reactor vials were first covered with aluminum foil for the first 10 minutes of analysis (FIG. 9) to block light from the light bulb generating about 50 μmol photons $m^{-2}\ s^{-1}$).

| Residues in the vicinity of the proximal delivery 4Fe—4S cluster | | | Residues in the vicinity of the proximal catalytic 4Fe—4S cluster | | |
| --- | --- | --- | --- | --- | --- |
| Sequence number | Amino acid | Distance between residue and the Fe—S cluster (Å) | Sequence number | Amino acid | Distance between residue and the Fe—S cluster (Å) |
| 140 | leu | 4.6 | 191 | leu | 6.0 |
| 156 | ala | 6.0 | 192 | leu | 6.0 |
| 158 | gly | 6.0 | 195 | gln | 6.0 |
| 160 | asn | 6.0 | 301 | pro | 4.9 |
| 161 | thr | 4.2 | 302 | gly | 5.3 |
| 163 | thr | 4.1 | 303 | trp | 5.8 |
| 164 | tyr | 6.0 | 354 | pro | 5.8 |
| 165 | ala | 4.1 | 356 | thr | 6.0 |
| 166 | met | 4.7 | 357 | ser | 4.2 |
| 185 | phe | 4.6 | 358 | lys | 4.7 |
| 189 | asn | 6.0 | 497 | met | 4.2 |
| 191 | leu | 4.0 | 498 | ala | 5.0 |
| 192 | leu | 6.0 | 502 | gly | 6.0 |
| 194 | gly | 4.5 | 504 | val | 6.0 |

-continued

| Residues in the vicinity of the proximal delivery 4Fe—4S cluster | | | Residues in the vicinity of the proximal catalytic 4Fe—4S cluster | | |
|---|---|---|---|---|---|
| Sequence number | Amino acid | Distance between residue and the Fe—S cluster (Å) | Sequence number | Amino acid | Distance between residue and the Fe—S cluster (Å) |
| 195 | gln | 6.0 | 505 | asn | 6.0 |
| 197 | ile | 6.0 | 506 | gly | 5.8 |
| 356 | thr | 6.0 | 507 | gly | 6.0 |
| | | | 508 | gly | 6.0 |

Table 1 indicates the residues evaluated for substituting the native residue with a Cys residue. The numbers indicate the approximate distance between the new residue and the closest Fe or S atom in the neighboring proximal 4Fe-4S cluster. Note that some residues appear in both tables.

TABLE 2

| Mutations around the PDC | | Mutations around the PCC | |
|---|---|---|---|
| Faster $H_2$ production | Higher $O_2$ tolerance | Faster $H_2$ production | Higher $O_2$ tolerance |
| A156C, | A156C, | P301C, | P301C, |
| G158C, | M166C, | T356C, | T356C, |
| M166C, | G194C, | M498C, | S357C |
| L192C, | Q195C, | N505C | |
| Q195C, | I197C, | P301C N505C, | P301C T356C, |
| G185C I197C, | A156C L191C | T356C S357C, | P301C A498C, |
| N160C L192C, | G158C I197C | S357A, | P301C G502C, |
| T163C Y164C, | N160C T161C, | S357V, | G302C T356C, |
| Y164C I197C, | N160C A165C, | S357I, | G302C S357C, |
| A165C L191C, | N160C L192C, | S357P, | G302C A498C, |
| L192E, | N160C Q195C, | T356V S357T, | W303C G507C, |
| L192G, | N160C I197C, | | P354C G508C, |
| | T161C G194C, | | T356C S357C, |
| | T161C I197C, | | S357C A498C, |
| | T163C N189C, | | S357C N505C, |
| | T163C Q195C, | | T356V, |
| | T163C I197C, | | T356I, |
| | Y164C Q195C, | | T356L, |
| | | | T356P, |
| | A165C N189C, | | S357A, |
| | A165C L192C, | | S357V, |
| | A165C Q195C, | | S357I, |
| | A165C I197C, | | S357L, |
| | M166C Q195C, | | S357T, |
| | M166C I197C, | | S357P, |
| | F185C I197C, | | T356V S357T, |
| | N189C G194C, | | T356V S357V, |
| | N189C I197C, | | T356V S357P |
| | L191C L192C, | | |
| | L191C I197C, | | |
| | Q195C I197C, | | |
| | L192F, | | |
| | L192W, | | |
| | L192S, | | |
| | L192D, | | |
| | L192G, | | |

Table listing all mutations around the PDC or PCC that significantly improved either the anaerobic $H_2$ production activity or $O_2$ tolerance of CpI.

Sites for amino acid substitution within CpI were chosen based on the distance to the closest Fe or S atom of the proximal 4Fe-4S cluster. A cutoff distance of about 6.5 angstrom was used. 17 sites were identified in vicinity of the PDC, and 18 around the PCC. 4 sites (L191, L192, Q195, and T356) were within the cutoff distance to both clusters.

Changes in $O_2$ tolerance were determined by mutating the residues surrounding the PDC or PCC into Cys. These single Cys replacement mutations around the PDC or PCC were combined to create CpI mutants with double Cys replacements. A few combinations of single Cys replacements caused synergistic improvement in $O_2$ tolerance. This information was used in selecting the sites for combining non-Cys replacements around the PDC or PCC as well for further improvement in $O_2$ tolerance.

Non-Cys replacements, e.g., L192G, were found that improved $O_2$ tolerance more than the highest level obtained with Cys replacements. Combinations of non-Cys replacements at T356 and S357 synergistically improved $O_2$ tolerance. The mutant with greatest $O_2$ tolerance had T356V and S357T substitutions.

What is claimed is:

1. A modified Fe—Fe hydrogenase comprising at least one amino acid substitution relative to the wild-type sequence, said modified Fe—Fe hydrogenase has
   [i] at least 80% sequence identity to SEQ ID NO: 1, and at least one amino acid substitution at L192, G194, T356 or S357;
   [ii] at least 96% sequence identity to SEQ ID NO: 2, and at least one amino acid substitution at L191, G193, N355 and/or D356;
   [iii] at least 80% sequence identity to SEQ ID NO: 3, and at least one amino acid substitution at L192, G194, T356 or A357;
   [iv] at least 80% sequence identity to SEQ ID NO: 4, and at least one amino acid substitution at L192, G194, T356 or A357; or
   [v] at least 80% sequence identity to SEQ ID NO: 5, and at least one amino acid substitution at L191, G193, N355 or D356;
   wherein the modified enzyme retains at least 10% of the initial specific activity following exposure to 0.01 atm. $O_2$ for 5 minutes.

2. The modified hydrogenase of claim 1, wherein the Fe—Fe hydrogenase is derived from a *Clostridium* species.

3. The modified hydrogenase of claim 1, wherein the amino acid substitution is selected from A156C, M166C, G194C, Q195C, I197C, A156C+L191C, G158C+I197C, N160C+T161C, N160C+A165C, N160C+L192C, N160C+Q195C, N160C+I197C, T161C+G194C, T161C+I197C, T163C+N189C, T163C+Q195C, T163C+I197C, Y164C+Q195C, A165C+N189C, A165C+L192C, A165C+Q195C, A165C+I197C, M166C+Q195C, M166C+I197C, F185C+I197C, N189C+G194C, N189C+I197C, L191C+L192C, L191C+I197C, Q195C+I197C, L192F, L192W, L192S, L192D, L192G, P301C, T356C, S357C, P301C+T356C, P301C+A498C, P301C+G502C, G302C+T356C, G302C+S357C, G302C+A498C, W303C+G507C, P354C+G508C, T356C+S357C, S357C+A498C, S357C+N505C, T356V, T356I, T356L, T356P, S357A, S357V, S357I, S357L, S357T, S357P, T356V+S357T, T356V+S357V, T356V+S357P, where numbering is made relative to SEQ ID NO:1.

4. The modified hydrogenase of claim 3, wherein the amino acid substitutions is one or more of L192G, G194C, T356V, S357T.

5. The modified hydrogenase of claim 4, wherein the hydrogenase comprises the amino acid sequence set forth in SEQ ID NO:6.

6. The modified hydrogenase of claim 3, wherein the at least one amino acid substitutions that provides for faster $H_2$ generation is selected from A156C, G158C, M166C, L192C, Q195C, G185C+I197C, N160C+L192C, T163C+Y164C, Y164C+I197C, A165C+L191C, L192E, L192G, P301C, T356C, M498C, N505C+P301C, N505C, T356C+S357C, S357A, S357V, S357I, S357P, T356V+S357T.

* * * * *